(12) United States Patent
Ehrlich et al.

(10) Patent No.: US 7,115,732 B2
(45) Date of Patent: Oct. 3, 2006

(54) **SELECTED NUCLEOTIDE SEQUENCES ISOLATED FROM PATHOGENIC STRAINS OF *HAEMOPHILUS INFLUENZAE***

(75) Inventors: Garth D. Ehrlich, Pittsburgh, PA (US); Patricia Antalis, Sewickley, PA (US); John Gladitz, Pittsburgh, PA (US); Geza Erdos, Wexford, PA (US); Fen Z. Hu, Pittsburgh, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 11/133,690

(22) Filed: May 20, 2005

(65) Prior Publication Data

US 2005/0267298 A1 Dec. 1, 2005

Related U.S. Application Data

(63) Continuation of application No. 10/698,235, filed on Oct. 31, 2003, now Pat. No. 6,969,762.

(51) Int. Cl.
    *C07H 21/04* (2006.01)
(52) U.S. Cl. ..................................................... 536/23.7
(58) Field of Classification Search ............... 536/23.7, 536/24.32; 424/256.1; 435/69.1
    See application file for complete search history.

(56) References Cited

OTHER PUBLICATIONS

Fleischmann et al. Jul. 1995. Science. 269: 496-512.*

* cited by examiner

*Primary Examiner*—Jennifer E. Graser
(74) *Attorney, Agent, or Firm*—Ansel M. Schwartz

(57) ABSTRACT

A DNA sequence of *Haemophilus influenzae* clone 151_04 shown in SEQ. ID. NO. 1. A DNA sequence of *Haemophilus influenzae* clone 125_L2 shown in SEQ. ID. NO. 2. A DNA sequence of *Haemophilus influenzae* clone 179_D14 shown in SEQ. ID. NO. 3. A DNA sequence of *Haemophilus influenzae* clone 167_A16 shown in SEQ. ID. NO. 4.

1 Claim, No Drawings

SELECTED NUCLEOTIDE SEQUENCES ISOLATED FROM PATHOGENIC STRAINS OF *HAEMOPHILUS INFLUENZAE*

This application is a continuation of application Ser. No. 10/698,235 filed on Oct. 31, 2003 now U.S. Pat. No. 6,969,762.

FIELD OF THE INVENTION

The present invention is related to *Haemophilus influenzae*. More specifically, the present invention is related to selected nucleotide sequences isolated from pathogenic strains of *Haemophilus influenzae*.

BACKGROUND OF THE INVENTION

*Haemophilus influenzae* is a naturally transformable gram-negative bacterial pathogen that colonizes both the upper and lower human respiratory tracts. In the upper respiratory tract it can colonize the nasopharynx and then spread locally to cause disease in the ears (otitis media), sinuses (sinusitis), and meninges (meningitis). In the lower respiratory tract *H. influenzae* is associated with chronic obstructive pulmonary disease (COPD), bronchitis, and pneumonia. *H. influenzae* is sometimes considered to be an opportunistic pathogen as invasion usually follows a loss of the mucocilliary escalator function following either viral or toxigenic denudement. (Swords, W. E., M. R. Ketterer, J. Shao, C. A. Campbell, J. N. Weiser, and M. A. Apicella. 2001. Binding of the non-typeable *Haemophilus influenzae* lipooligosaccharide to the PAF receptor initiates host cell signalling. Cell. Microbiol. 3:525–536, incorporated by reference herein.) *H. influenzae* is associated with both acute and chronic infections for which it has developed specialized survival strategies.

The entire genome of the less virulent laboratory reference strain of *H. influenzae*, designated Rd, was sequenced and published in 1995-(Fleischmann et al., Science 269: 496–512). However, since many of the genes that are responsible for the virulence of *H. influenzae* are missing from strain Rd, the sequence of the Rd genome is insufficient for developing tools to detect or prevent *H. influenzae* infections.

*H. influenzae* strains are classified according to their expression, or lack of expression, of a polysaccharide capsule. Encapsulated isolates are divided into six antigenic serotypes (a–f), whereas nonencapsulated isolates are classified as nontypeable *H. influenzae* (NTHi). *H. influenzae* type b (Hib) is associated with invasive disease and was previously responsible for the vast majority of *H. influenzae*-associated cases of meningitis. The introduction of an Hib vaccine in 1985 greatly decreased the incidence of type b infections (Scheifele, D. W., T. P. Jadavji, B. J. Law, R. Gold, N. E. Macdonald, M. H. Lebel, E. L. Mills, P. Dery, S. A. Halperin, R. F. Morris, V. Marchessault, and P. J. Duclos. 1996. Recent trends in pediatric *Haemophilus influenzae* type b infections in Canada. Can. Med. Assoc. J. 154:1041–1047; Schulte, E. E., G. S. Birkhead, S. F. Kondracki, and D. L. Morse. 1994. Patterns of *Haemophilus influenzae* type b invasive disease in New York State, 1987–1991: the role of vaccination requirements for daycare attendance. Pediatrics 94:1014–1016, both of which are incorporated by reference herein); however, non-type b strains, including the NTHi, continue to be important pathogens worldwide.

Most strains of *H. influenzae* are naturally competent, with the ability to take up DNA from their environments and integrate it into their chromosomes. Many naturally competent bacteria such as *Haemophilus* sp. and *Neisseria* sp. preferentially take up DNA from highly related organisms, which they recognize by the presence of genera-specific conserved uptake signal sequences (USSs) that are over-represented in their respective genomes (Elkins, C., C. E. Thomas, H. S. Seifert, and P. F. Sparling. 1991. Species-specific uptake of DNA by gonococci is mediated by a 10-base-pair sequence. J. Bacteriol. 173:3911–3913; Mathis, L. S., and J. J. Scocca. 1982. *Haemophilus influenzae* and *Neisseria gonorrhoeae* recognize different specificity determinants in the DNA uptake step of genetic transformation. J. Gen. Microbiol. 128:1159–1161; Smith, H. O., J.-F. Tomb, B. A. Dougherty, R. D. Fleischmann, and J. C. Venter. 1995. Frequency and distribution of DNA uptake signal sequences in the *Haemophilus influenze* Rd genome. Science 269:538–540, all of which are incorporated by reference herein). The *H. influenzae* Rd genome contains 1465 copies of the hUSS (Smith, H. O., J.-F. Tomb, B. A. Dougherty, R. D. Fleischmann, and J. C. Venter. 1995. Frequency and distribution of DNA uptake signal sequences in the *Haemophilus influenze* Rd genome. Science. 269: 538–540, incorporated by reference herein); thus, on average, there is about one hUSS per 1200 bases, or approximately one/gene. This frequency of the hUSS would theoretically provide for the exchange of any *H. influenzae* gene among strains. Thus, the natural transformation system of *H. influenzae* provides a mechanism for generating multiple types of genetic diversity among strains, including genetic heterogeneity (allelic differences) and genomic plasticity (genic differences).

There is evidence that inter-species transfers occur as well. Kroll et al. (Kroll, J. S., K. E. Wilks, J. L. Farrant, and P. R. Langford. 1998. Natural genetic exchange between *Haemophilus* and *Neisseria*: intergeneric transfer of chromosomal genes between major human pathogens. Proc. Natl. Acad. Sci. USA 95:12381–12385, incorporated by reference herein) have presented evidence of uptake sequence-mediated intergeneric transfer between the upper respiratory pathogens *Haemophilus* and *Neisseria*. These researchers identified three regions of *Haemophilus*-like DNA in the *Neissera meningitidis* genome and suggested that transformation with heterologous DNA may play an important role in establishing chromosomal mosaicism in these organisms.

Several studies have shown that chronic NTHi infections display significant genetic and phenotypic diversity (Loos, B. G., J. M. Bernstein, D. M. Dryja, T. F. Murphy, and D. P. Dickinson. 1989. Determination of the epidemiology and transmission of nontypeable *Haemophilus influenzae* in children with otitis media by comparison of total genomic DNA restriction fingerprints. Infect. Immun. 57:2751–2757; Porras, O., D. A. Caugant, B. Gray, T. Lagerigard, B. R. Levin, and C. Svanborg-Eden. 1986. Difference in structure between type; van Alphen, L., D. A. Caugant, B. Duim, M. O'Rourke, and L. D. Bowler. 1997. Differences in genetic diversity of nonencapsulated *Haemophilus influenzae* from various diseases. Microbiology 143:1423–1431, all of which are incorporated by reference herein). van Alphen et al. used multilocus enzyme electrophoresis to examine the genetic diversity among 80 isolates of NTHi recovered from both healthy patients and those presenting with different diseases. These researchers concluded that chronic persistence in the host contributes to the genetic diversity of NTHi.

To examine the degree of genomic plasticity among pathogenic strains of *H. influenzae*, a highly redundant, pooled genomic library was generated using hydrodynamically sheared DNA from 10 clinical isolates cultured from pediatric patients undergoing treatment for chronic otitis media with effusion. This library is also being used as part of a larger investigation to study gene expression in order to delineate the genetic control of biofilm formation in pathogenic strains of *H. influenzae*. The present invention addresses the objective of evaluating the genomic plasticity between the nonpathogenic *H. influenzae* reference strain Rd and 10 clinical isolates, and DNA sequence evidence that reveals an extensive degree of plasticity among all strains.

The present invention involves isolated and cloned novel DNA fragments that are present in pathogenic strains of *Haemophilus influenzae* (cultured from pediatric patients undergoing treatment for chronic otitis media with effusion) and are absent in strain Rd. Four of these sequences are disclosed, whose corresponding amino acid sequences display varying degrees of homology to virulence-associated bacterial proteins.

SUMMARY OF THE INVENTION

The present invention pertains to a DNA sequence of *Haemophilus influenzae* clone 151_04 shown in SEQ. ID. NO. 1.

The present invention pertains to a DNA sequence of *Haemophilus influenzae* clone 125_L2 shown in SEQ. ID. NO. 2.

The present invention pertains to a DNA sequence of *Haemophilus influenzae* clone 179_D 14 shown in SEQ. ID. NO. 3.

The present invention pertains to a DNA sequence of *Haemophilus influenzae* clone 167_A16 shown in SEQ. ID. NO. 4.

DETAILED DESCRIPTION

The present invention pertains to a DNA sequence of *Haemophilus influenzae* clone 151_04 shown in SEQ. ID. NO. 1.

The present invention pertains to a DNA sequence of *Haemophilus influenzae* clone 125_L2 shown in SEQ. ID. NO. 2.

The present invention pertains to a DNA sequence of *Haemophilus influenzae* clone 179_D14 shown in SEQ. ID. NO. 3.

The present invention pertains to a DNA sequence of *Haemophilus influenzae* clone 167_A16 shown in SEQ. ID. NO. 4.

Referring more specifically to these DNA sequences:

(1) Clone 151_O4

Clone 151_O4 contains a novel DNA sequence found in every one of the 10 pathogenic *Haemophilus influenzae* isolates. The most significant stretch of homology displayed by this novel nucleotide sequence is a stretch of 110 bp with 76% homology to the related bacterium *Pasteurella multocida* (May et al., 2001). The full-length, putative protein encoded by the novel 1337 bp sequence exhibits homology (47% identical, 68% similar) to the YhbX/YhjW/YijP/YjdB family protein in the bacterial pathogen *Neisseria meningitidis* (Tettelin et al, 2000). This meningococcal protein is named for its homology to a group of probable membrane-associated proteins originally identified in *E. coli*. Most interesting is the *E. coli* YijP protein, which is involved in the penetration of the blood-brain barrier and thereby contributes to the pathogenesis of *E. coli* meningitis (Wang et al., 1999). Also noteworthy is a tract of six copies of the tetranucleotide TITG that occurs within the first 150 nt of the putative open reading frame (ORF). Tetranucleotide repeats have been associated with virulence genes in *H. influenzae* (Hood et al., 1996, Ren et al., 1999).

Nucleotide sequence of *H. influenzae* clone 151_O4. The novel 1337 bp sequence that is being disclosed is underlined.

AGTAATATCACAATAGSGGATCCACGAGCTTCTATTAGGTATCGTATTGG

CTGCAGAGGGATATCCAAAGGATTATCGCAAAGGCGATGAAATCAGCGGA

TTGCCTAAAAGTGCGGTCAAAAACGAGAAAGTTTTCTTAGCGGGTGTCGC

AGAACAAGAAGGCAAGCTAGTCACAAACGGCGGTCGTGTACTTTGTGTGA

CTGCGTTAGGCGAAAGTGTATTTGAAGCACAACAAAAAGCGTTAAAATTG

GCTGAGCAAATTCAATGGTCTGGGCGTTTTTATCGTCGAGACATTGGTTA

CAGGGCTGTGGAACGAGA<u>ACAAGCAAAATAGTTAGAAATCTTGTTTGAAT</u>

<u>TTAATTAGATAAAAATATTGTACAGGGTAGAATTGTATTTTCCTAGGAT</u>

<u>TTAGGATTTTGTTAGGGCAACGTTTACGATTGCTCTGACAATAAATTAGA</u>

<u>ATTATTATTTTTGTTACTTTATGAGGTTATATCAACTTATGCGACAATTT</u>

<u>GTCATCGTAGTATTATATTCTGCAATTCTTCTTTCATTAGAAGTTATTTA</u>

<u>TAGAAAATTATTTAATATTTCTAGTATTGAGAGATACACTGAAAGTTATT</u>

<u>TGTCTGTTTGTTTGTTTGTTTGTTTGTTTTTTCAAAATATAGAATT</u>

<u>ACAAGAATATTAGTTGGCGCTTTATTTGCAATAAGTATTGTTGTTAATAA</u>

<u>TGTACATTATGCAGTATACCAATCTTGGATTGGACCTGTTAATTACTCAC</u>

<u>TTGCATTTAAAGAAATTAATGAGATAACAAATGCTGGCTTAACAATGATA</u>

<u>GATAAATTCATATATCCATTGTTATTTGGTTTATTTGAAGTTGCTGTGTT</u>

<u>TTTAAGTTTAAGTTTCATAAAAAGAAAAGTATATAAACTTTCTTGGATTT</u>

<u>TTGACTTTATTTTTTATGCTGTGATGATGTATGTTTTTGTTCGAGCGTAT</u>

<u>ACAACAAAATCCCATGAGCGTTTTATTTCACCTAACACTGTTTATTCTCG</u>

<u>ATTAAAATCCAATTATTTATCGTTGGGTTATTTTATAGGACGAATTGTTC</u>

<u>CTTATGAGATATTTTCTTTATCTAATATTCCTCTTTATCATAAATCTAAG</u>

<u>CCTATGAAATCGGGCTCTCCGVAAAATTMARGAATATAATTTTAATTAAT</u>

<u>GGGGGAAAGTGCGACCTCAAGTCATTTTAGTGCTTTTGGTTACGGGAGAA</u>

<u>AAACATCTCCTTTTTTAGATAGCTTAAAATATAAATCAGGAGCTCTTGTT</u>

<u>GGTAAAACTTATTCAGGAGGAAAGCTAACAGCAATTTCTTTACCAATGTT</u>

<u>TTTTAATGCAATYCCTTAYCCAAATGGAATACAACAGATAGCTAAAGGAG</u>

<u>ATACGAATTTATTTAATTTAGCGAAAGAGCAAGGCTTTCAGACATATTTT</u>

<u>TATTCAGCTCAAGCTAGGGATGATATGCATATGATCAATTTTTTAGGAGG</u>

<u>AGCTTGGATTGATGATATTCGTTTTCCAGATAATGAAGGGTATTCTTTAA</u>

<u>GAGATTCAATGCCTGATAATAAATTACTTCCTGCTTTTAAAAATATTAAT</u>

<u>TTAGATAATGGTTATCATTTTGTTGTTTTACATCATAGAGGGAGTCATAT</u>

<u>TCCCTATGGGCATTATTAGAATGAAAAAGNAGNAAGGTGTTKGGAARAA</u>

<u>ATAACG</u>

(2) Clone 125_L2

The 1,802-bp cloned *H. influenzae* fragment in 125_L2 is a novel polynucleotide that is found in 9 of th 10 pathogenic

*Haemophilus influenzae* isolates. Sequence similarity searches revealed only two short regions (approximately 75 bp each) that display nucleotide homology (83%) to the *Shigella* resistance locus (SRL) pathogenicity island (PAI) of *S. flexneri* serotype 2a. The 66,257-bp SRL PAI carries genes for antibiotic resistance, iron uptake, and at least 22 prophage-related ORFs (Luck et al., 2001). The conceptual translation of the 125_L2 sequence and subsequent homology search revealed 3 open reading frames (one complete, two incomplete). All three inferred protein products of this clone were homologous to the proteins encoded by ORFs 7, 8 and 9 of the SRL PAI (Luck et al., 2001). These *Shigella* homologs included a probable LysR-like transcriptional regulator (ORF 7; 64% identical, 73% similar), an unknown protein (ORF 8; 58%, 78%), and a putative anaerobic decarboxylate transporter (ORF 9; 54% identical, 64% similar).

Nucleotide sequence being disclosed for clone 125_L2.

CCTGCAACAGCTAGCTGAGATGATACAACCGATCCCGATAAAACTCTGGA

TGGTCTAATTCCAGATTCTTTTGCAACTTCAGCAATGACAGGTAATGTAG

AAAAAACAATAAATCCAGTACCTGCAAAAATGGTCATTAACCAAGTAATC

ATTGGCGCAATAAAATTTATATGTTTGGGRTTTTTACGSATTAATCTTTC

TGCATAATTAACTAAGRATGCCATTCCCCCTGTAGCTTGCAATGTTGCTG

CTGRAAGRGRTACAGACATTATGRTCAAAATAACATCTATTGGRACAGRT

CCTATTGGTAGTCTTAAACCCAACGTTAAGRTAGCAAGTCCAAGACCACC

AAATAAACCAATGGCAATACCTCCAAATCTAAGGCCAAGTACAATAGAGG

CTAGARCAACAAARATTTCAACCCMGACCATAATCATCTCCTTAATCAAT

GTTTGATACCAACGMATAGCAGCTCTAACTAATGCTGCTGTAGARTCCTC

ATAAAGTATAGGTTGCTCTCTCATTGCATTTTTTAGGATCARTGGGATTT

CCGTACACCCTAGAATAATNACTTCTGAACCGTGACGAATAACTTCATCA

CGTTGTATTAACATTAATTCTTCAGCTTTTTGAATCTCTCCGCTCTTATA

TAAATAAATACTTTCCATGACCGATTTTTGATGTTCTTCATTGGGAAGAA

GACAAATTAATTCCATATTTTTCTAATGTTTTCTGATATAGCTTTGTTGC

TAAAGTAGCATCAGTAGCAAGAATACCAATCTTTGTTTTACCCATTTGTA

GAACTTCATTAATTGTTGAATCAATAATATTTAACATATCAACATGACAT

TTCTCTTTTAGTTCATCATACCAATAATGTGCAGTATTACAGGCAATTAG

GATACATTTAGCACCCGCATTTTCTAACCCATAAATGCGTTCCTCCATTG

CAAGTAGTGGTGATTCTCCTCCATGCAAAATGGAAGTTGTACGATCGGGA

ATATCAGGAATAGACGAAATAACAAGAGGAATATGTTCTTGATCACAATG

AGCTGGTGTAAATTGAATAAATTTCTGAAACATATCTGCCGTTGCTGCTG

GTCCCATTCCACCTAAAATACCAATAATGTTCTTCATAAGAAAAATTCTC

CTATTTATCTTTGGGTTATTTATTTTTAACAAAATCTAATGAAATAAGAG

AAATGCAACAAATCGCACGCCAATGCAAATATTGCATAGCATAAATTGCG

CACATTACAAATGTACAAAATAATGATTCAAATCAATATGATAAAAAACA

AAAAGTGATAAGCTATTACATATTTAAGAATAAGGTATGCAAAATTAGCA

TAGAGAGAAATAATAAATGAAAAATATTGAAACAAAATGGTKAGAAGATB

TTTTAATACTGGAAGATACACGCAATTTTTCACAGGCAGCAGAACATAGA

AATTTATCGCAATCAGCTTTTAGCCGGAGAATAATTTCTCTTGAAGAATC

TATTGGTGTAAAACYCTYCGATAGAYCCTCTGYCCCACTTCAACTTACAG

AAGAAGGAAAATTATTTCATYCGCAAGHCTAGAAACCTTTTAAAACAGTT

ACAGTATAATCTTGATGAATTATTAGGGCAGAATACACAAAAAAACCGAA

TATAACTTTTGCAGCTGCACATTCCCTATCTTTATCTGTAATGCCAAAGT

TAATTCATGATATTGGTCAATCACACCAGAACTTTATTTATTCCGTTGAA

GCAATTGATGTTGATCAAACAGTAAAAACTTTGGTTGAAGGAAAAAGTGA (3) Clone 179_D14

This 950 bp polynucleotide is present in all 10 of the pathogenic *Haemophilus influenzae* isolates. It is highly homologous (88%) to the trbB gene of the phytopathogen *Ralstonia solanacearum*, and its deduced amino acid sequence is 91% identical to the *R. solanacearum* probable conjugal transfer protein TrbB (Salanoubat et al., 2002). TrbB belongs to an extensive superfamily of proteins involved in the formation of surface-associated protein complexes that mediate a number of diverse processes such as pilus biosynthesis, DNA transport, and the secretion of virulence factors (Whitchurch et al, 1990; Hobbs and Mattick, 1993). This superfamily encompasses both archeal and bacterial proteins and includes the subfamily of type IV NTPases to which TrbB proteins belong (Planet et al., 2001). Potentially noteworthy is the presence of a pentanucleotide repeat (CCGGC) that repeats three times and is located within the putative open reading frame. The strong DNA homology of this clone to *R. solanacearum*, and its extraordinarily high G+C (68%) content compared to that of *Haemophilus* DNA (38%), suggests that this DNA was recently acquired by *H. influenzae*.

Nucleotide sequence being disclosed for clone 179_D14.

TGGAAGTGATGCTCNACCCCGACCGGACATTGTGGGTGGATCGGCTGTCG

TCTGGCCGTGCGCCGCTCGGCGTCGAACTGCCCGAAGCCGATGGCGAACGCATCAT

GGCGGTGGTCGCCGCCCATGTCGGTGCGGAGGTGCATCGCGGCCAACCGCTCTTGA

CCGCCGAACTGCCTGAAACCGGCGAACGCTTCGAGGGCATCCTGCCGCCCGCCGCA

CCCGGCCCGGCCCGGCCTTTGCGCTGCGCAAGCGTGCCGTGAGCATCATCGGTCTG

GATCGCTATGTGGCTGATGGCATCCTGACCACTGGGCAGGCCGAGTTTCTGCGTCA

```
TGCCGTGCGCGAGCGGCACAACATCCTGATCGCCGGAGGCACCAGCACCGGCAAGA

CCACGCTGGCCAATGCCTTGCTGGCCGAGATCGCCGCCACCGGCGACCGCGTGCTG

GTGCTCGAAGACACCATCGAACTGCAATGCGCGGCCCGCGACCATGTGCCGCTGCG

CACCCGCGCCGGCGTCGTGTCCATGACCGAGCTGGTGCGGGCCACGATGCGCCTGC

GGCCCGACCGCGTGATCGTCGGCGAAGTGCGCGGCGGCGAAGCGCTGGATCTGGTG

AAGGTCTGGGGCACCGGCCACCCCGGCGGCATCGCCACCATTCATGCCGGCTCCGC

GTTGGGCGCGCTGCTGCGCCTGGAGCAACTGATCCTCGAAGTGGCGGTGAATCCGC

CCCGCGCCCTGATCGCCGAGGCGGTCAATGTCGTGATCCACATCGCAGGCCGCGGC

CGCAAGCGCCACGTCGAAACCATTTCCCGCGTCGTCGGTTTCGACGGCGCGGGCTA

CCGCCTGGCGGATGCGCTGGAAGCGACGCTTCCCGAGCTGCCGCCGGTTCCTCTTA

CAGCCGCTGCCGCTACGCCTTCCTCGATCCCTGAACAACCTGGAGAACTGCCATGA

CGCA
```

Clone 167_A16

The nucleotide sequence of clone 167_A16 is 2,597 nt in length and is present in 4 of our clinical *H. influenzae* strains. It displays two short regions of 55 and 60 nt with homology (96% and 90%, respectively) to Rd. The remaining sequence displays no significant homologies to any known DNA sequence. The proposed amino acid sequence suggests that this clone encodes at least one protein with a tetratricopeptide repeat (TPR) motif. The tetratricopeptide repeat, which has been identified in a wide variety of proteins, is a structural motif that mediates protein-protein interaction (Blatch and Lassle, 1999). The proteins with the highest homologies (based on computer analysis) to the TPR protein encoded by 167_A16 are almost exclusively from bacterial pathogens. Many of these homologs are, themselves, hypothetical proteins with unknown functions, including the *Haemophilus somnus* protein displaying the greatest homology (42% identical; 60% similar). A few homologs, however, have assigned functions that indicate the potential significance of this protein in *H. influenzae*. Included in these are the *Legionella pneumophila* enhanced entry protein (enhC gene product), which is involved in entry into host cells, and a *Helicobacter pylori* antigen (protein H) that granted significant protection against *H. pylori* challenge in a mouse model system (Cirillo et al., 2000; Hocking et al, 1999).

Downstream of the putative open reading frame for the TPR protein, another region was analyzed that appears to have a very weakly conserved TPR motif Its primary homolog is a conserved hypothetical *H. pylori* protein. Finally, the hypothetical translation of a third putative coding region shows no evidence of a TPR motif and has its highest homology to a *Listeria monocytogenes* protein that is similar to the putative integral membrane protein, ComEC, which is required for DNA uptake (Glaser, et al., 2001).

Nucleotide sequence being disclosed for clone 167_A16.

```
TTTGATTGAGCTCACGATATTTATCACACCCTTCTTGACTACGTAGATCG

CAAGCCATGCCATAGTAAGATTTAGCTTTTTGCTCATCTTTATAAAGAAA

CGCGTTCCCTAATTCCACAAACACTGCAGGATCTTGGCTATTTTCCAATT

CTAATTGCAATGTTTCAAATTTTGCTTTTACATCATCATTCGGCGCCTCA

TCTTTTAATTTTTTTAATTTTATTAACTTCACCTTTGTACCAATCACTGT

CATTTCATCTTTAGTTTCTTTATTATGCTCTTGCAATAATTGCTCGGCTT

TATTTTCATCTTTTACCGTGCCAATTCCCAAAATATAAAGAATAGCTAAT

TCACGATAAACGCTATTTGGACGAAATCGATTATTTTCTACTTGTCTAAA

CACCGCAGGTTGATGGTGTAATAGACTGCTTTTATAGGCTTTATCCAACC

AATAAAAGCGGTTTTCCCAATCTGGTTTAATATTATCATTACCATCAAAA

TACCAACGCCCTAACTGTGCTTCCGCCATTGGATAACCATTATTTGCGGC

TTGTTCCACCAACATATAACCTGTCAAAAAATCCTTATCCTTATTTACGG

CATCTATAGMCAAGAATCATTTTGGCAAAATTATCGCCCGCATCCGCAGC

CATTTTCATATAATGTTTTGACGATTCTTTATTTCCTTTGTCATTATAAA

TGGTTGCCAAACCACGATATGCCAACGGATAATTTTGATTGCTGGCTTTA

AGAAACCACTCTGTCGCTAAATTTTTTTGACCTWTGATAAAATAATAACG

CCCCAACTGATATTGCGTCACAGCATTGCCTTTTTCATGCCAACACTCGC

AAACGTGCTGGAGAAAAATCTTCAAGTGCTTTNTCTAGCTTGCTGATCGC

CATAATACTCCTGAGCACTAACTAATMVTTCTAGCTGTTTAATCTCACGA

TATTCTGGGTAATATTGGGTAAAATACACAGCTCCACCACCAATTACTGC

CAATAATAAAACGGCTAAGGTTAATTTTTTCTTCATTATTTTGTTCCTTG

ATTTAATTGTTTATACATCTCACAACCTTTTTGCTCTTTATTATCACAAG

CCTTGCCAAACCATTTTTTGGCAGTGGCAAAATTTTGTTTTACTCCTATT

CCGCCCATATAAGCAAGACCAACTATTGCCTGCGCTCGAGAATTATTATT

TTCTGCTGCTTTTTGATACCATTTTATGGCTTCAGTTTTATTTTCTTTTA

CTCCATCGCCATCATAATACATATCGCCCAATATCATTTGGGATTCAGTA

TCATTTTGATTTGCCGCTTTTTTCAACCATTTCACTGCTTCCGTATTATT

CTGTTTTACGCCAACTCCATCTTTATACATCATTCCCACTTTAAATTGGG
```

-continued

```
CATCAACATCATCTTGCTCCGCAGCTTCCTTCAACCATTTAAAGCCTTCT

TGGTAATTTTGTTTTACGCCCAAGCCGTTAATATACATACCAGCTAAATC

ATATTGAGCGATACGTACACCTTGTTCAGCCGATTTTTTATACCATTTTA

TCGCTTCAAAATAATCTTGCTTTATGCCATCGCCATTTTTATATAACACC

GCTAACATCCCCTGTGCAATCCCATCTCCCTGCTCTGCTAAAGGACGAAT

AATTGCTAATGCGGACTTAAAATCTTTCTGTTCAAATAAATGAACAATCT

TATCAACTTGCTCCTCTTCCATTGCATAAACGGTTGATTGAAAAGAAAAG

ATAGAAGCACCGAAAAGTGCGGTGGTAAGAAGTGTTTTTGTTAGTTTCAT

TTTGTTTTCCTATTAAATTGAATGAATAAATAATCTTTTATTTTTATTCA

CTAAAATTGGCGTATAAGTAGAAAAATCTTTAAGTACTTCGCTATGTGGG

TGCCCATTTCGTCGCTGGCTATCTGCTGAAAACACACTAAGACAAGGCGA

AAATATGTTCGCTAATCCTTGCTGCCAATTATGCTTTGAACCGTGATGGG

GAACTTGTAAGCMATMAATYSTSGCCATTCGTTCTACACCTAATGATTGC

GTTAAATCGGTTAATAATGGCAAATCATTTAAAAACGCATCGCCTGTATA

TAAAATCGCATTTTTGTTTCTATCTTTTGGGAAAACAAGAATTTCATTTC

CATCATTTTTAGGAATATCATAAATATAATTATTCCCTAGTCCCCAAACA

GCTGTTGATGTTATATTTCTAATATATAAATATTGAGAAATGATATTTTT

GTTTTTATTTCCATTTCCAAATGCGAGAGTATAGAGTGTTTTTAAGGCTG

GCGTTGGATCTGTGGAATTAGACTGATGAGATTGAATAATTTGCTCAACC

TGCTTTTGAAAAGCAGTCAAATTTGTTGGCACTTTTGCAAGCAAATGAAA

TGGCACGTTATATAAAACAAATTCAAACTGCTCTTCGCCTTTTCTAAATA

AAAGGGCTTTATCAGGATTGAGCCAATGTACATTTTGTTTTAAGTTATCA

AACTCATTTGATAATTTTTCAGTAGTTTTAAAAGAAAGTACATCATCAAA

ATTACTTGGTTCAAGAGTTATCAAAATTTCACTCTCATTTTCTTTTG
```

Since the genes that are responsible for the virulence of *H. influenzae* are missing from strain Rd, the sequence of the Rd genome is insufficient for developing tools to detect or prevent *H. influenzae* infections. The sequences identified herein were characterized based on their absence in strain Rd, their presence in pathogenic strains of *H. influenzae*, and their significant homologies (at the amino acid level) to proteins implicated in bacterial pathogenesis.

In the operation of the invention, ten strains of *H. influenzae*, cultured from pediatric middle-ear effusions at Children's Hospital of Pittsburgh, were obtained as pure first-plate isolates on chocolate agar. These strains, designated AA–JJ, were typed serologically using slide agglutination at the Pittsburgh Public Health Laboratory. All specimens were tested initially with poly a–f antiserum (Difco Laboratories, Detroit, Mich.). Specimens giving a positive reaction were then tested with anti-a antiserum and anti-b antiserum. (Antisera specific for the less common serotypes c, d, e and f were not available at this facility.) Strain AA was classified as an encapsulated strain of serotype c, d, e, or f. The nine remaining clinical isolates (BB–JJ) were classified as non-typeable strains of *H. influenzae*.

Bacterial Growth Conditions. *H. influenzae* strains were grown in Brain Heart Infusion broth (Becton Dickinson, Sparks, Md.) supplemented with hemin (final concentration of 10 µg/ml; Fisher Scientific, Pittsburgh, Pa.), NAD (final concentration 2 µg/ml; Sigma, St. Louis, Mo.), and thiamine HCl (final concentration 20 µg/ml; Sigma) at 37° C. in a 5% $CO_2$ atmosphere for one passage followed by storage in 22% glycerol at −80° C. *E. coli* TOP 10 cells was grown in Luria-Bertani broth or on Luria-Bertani agar (Becton Dickinson, Sparks, Md.) at 37° C. Kanamycin (Invitrogen, Carlsbad, Calif.) was added to a final concentration of 50 µg/ml when necessary for selection.

Isolation of Bacterial Genomic DNA. Genomic DNA was extracted from each clinical strain using a modification of the method described in Ausubel et al. (Ausubel, F. M., R. Brent, R. E. Kingston, D. D. Moore, J. G. Seidman, J. A. Smith, and K. Struhl. 1990. Current protocols in molecular biology. Greene Publishing Associates and Wiley-Interscience, New York, N.Y., incorporated by reference herein.) Cells were collected by centrifugation from 100 ml overnight cultures and were resuspended in TE buffer (10 mM Tris-HCl, pH 8.0, 1 mM EDTA, pH 8.0). The cells were lysed by the addition of sodium dodecyl sulfate (SDS; Invitrogen) to a final concentration of 0.5% and incubated at 37° C. for one hour with RNAse A (final concentration 50 µg/ml; Gentra Systems, Inc., Minneapolis, Minn.). Cellular proteins were removed with Proteinase K (final concentration 100 µg/ml; Invitrogen) at 37° C. for 1 h. Cetyltrimethylammonium bromide (CTAB; Sigma) was added to a final concentration of 1%, and samples were incubated at 65° C. for 20 min. Following a chloroform/isoamyl alcohol (24:1) extraction, the DNA was precipitated from the aqueous phase with 0.6 volumes of isopropanol. The DNA was pelleted by centrifugation and washed with 70% ethanol. After air drying, the pellets were resuspended in TE buffer at 65° C. for 1 h. The samples were quantitated using UV spectrophotometry and their quality analyzed by agarose gel electrophoresis.

Construction of pooled genomic library. A library of pooled genomic DNA was constructed primarily to diminish the experimental bias that might have resulted from a single-strain library. The genomic DNA from each clinical isolate was fragmented in the HydroShear™ (GeneMachines, San Carlos, Calif.) by following the manufacturer's instructions for obtaining DNA fragments with an average length of 1.5 kb (range 1.0–2.5 kb). Aliquots (10 µg each) of the sheared DNA preparations were pooled, end-repaired, ligated into the plasmid pCR®4Blunt-TOPO and transformed into *E. coli* TOP10 all according to the manufacturer's protocol (Invitrogen, Corp., Carlsbad, Calif.). A detailed description of the library construction is presented elsewhere (Erdos, G. S., S. Sayeed, P. Antalis, F. Z. Hu, J. Hayes, J. Goodwin, R. Dopico, J. C. Post, and G. D. Ehrlich. 2003. Development and characterization of a pooled *Haemophilus influenzae* genomic library for the evaluation of gene expression changes associated with mucosal biofilm formation in otits media. Int. J. Pediatr. Otorhinolaryngol., 67:749–755, incorporated by reference herein). Briefly, the Q-bot 3-Axis XYZ Multi-Tasking Robot (Genetix Limited, UK) was used to array 76,800 transformants to construct the pooled *H. influenzae* library, which was stored in 10% glycerol at −80° C. Clones in the library were chosen randomly for further analysis.

DNA sequencing. Plasmid DNA templates were prepared for sequencing using the QIAprep Miniprep Kit (Qiagen, Inc., Valencia, Calif.). Prior to sequencing, plasmid preparations were digested with EcoRI (Invitrogen) and analyzed on ethidium bromide-stained 1% agarose gels in TAE buffer. Only those constructs containing insertions of *H. influenzae* DNA that appeared to be larger than 0.5 kb were used as sequencing templates. The LiCor $IR^2$ Gene ReadIR™ and the Beckman Coulter CEQ 2000 XL automated fluorescence sequencing systems were used to sequence the clones.

Sequencing reactions for the LiCor IR$^2$ Gene ReadIR™ DNA Analysis System were prepared according to the Excel II Simultaneous Bi-Directional Cycle Sequencing protocol provided by Li-Cor, Inc. (Lincoln, Nebr.). SeqiTherm Excel II DNA Sequencing Kits were purchased from Epicentre Technologies (Madison, Wis.). Fluorescent dye-labeled M13 and T7 primers (Table 1) were synthesized by L1-Cor, Inc. Sequencing reactions were carried out in Perkin Elmer 9600 thermal cyclers and included an initial 2-minute denaturation step at 94° C., followed by 40 cycles with a 30-s denaturation step at 92° C., a 15-s primer annealing step at 55° C., and an extension step of 15 s at 70° C. The final cycle was followed by storage at 4° C. Sequencing gels were prepared using 6% Long Ranger gel solution (BioWhittaker Molecular Applications, Rockland, Me.), 7M urea (Invitrogen), and 1.2×TBE (Invitrogen). Sequences were culled with Base ImagIR™ V.4.0 computer software (Li-Cor).

Sequence reactions for the Beckman Coulter CEQ 2000 XL DNA Analysis System were prepared using the CEQ 2000 Dye Terminator Cycle Sequencing with Quick Start Kit (Beckman Coulter, Inc., Fullerton, Calif.). Both unlabeled M13 and T7 primers, and specific primers for unique internal sequences of the *H. influenzae* cloned fragments were synthesized (Invitrogen) (Table 1). Cycling conditions were as follows: 30 cycles with a 20-s denaturation step at 96° C.; a 20-s annealing step at 50° C.; an extension step of 2 min at 60° C.; and a hold at 4° C. Ethanol precipitation was performed in an Allegra-25R centrifuge.

DNA sequence analysis. Sequences were analyzed and contig sequences were formed using Sequencher version 4.0.5 software package (Gene Codes Corporation, Ann Arbor, Mich.). DNA sequence similarity searches using the basic BLASTn and BLASTx algorithms (Altschul, S. F., W. Gish, W. Miller, E. W. Myers, and D. J. Lipman. 1990. Basic local alignment search tool. J. Mol. Biol. 215:403–410, incorporated by reference herein) were performed at the National Center for Biotechnology Information website (http://www.ncbi.nlm.nih.gov/).

Codon usage analysis of nonRd sequences. Published codon usage tables were obtained from the Kazusa DNA Research Institute website (http://www.kazusa.or.jp/codon/) (Nakamura, Y., T. Gojobori, and T. Ikemura. 2000. Codon usage tabulated from the international DNA sequence databases: status for the year 2000. Nucl. Acids Res. 28:292, incorporated by reference herein). The least squares optimization method (Cox, S. R., and D. E. Williams. 1981. Representation of the molecular electrostatic potential by a net atomic charge model. J. Comput. Chem. 2:304–323, incorporated by reference herein) was applied to the sequences of a set of genes from the *Haemophilus* Rd genome to confirm that it could distinguish *Haemophilus*-like codon usage from that of other organisms (J. Gladitz et al., manuscript in preparation). This method was then used to fit the codon usage of putative reading frames to the reported codon usage of the 71 organisms listed in Table 2. These particular organisms, which include prokaryotes, eukaryotes, phage and viruses, were selected on the basis that their genomes provided a continuous spectrum of G+C contents ranging from 24.62% to 67.67% (Table 2). In addition, many of these organisms encode proteins that display homology to the conceptual translations of our nonRd sequences.

The above process involved optimizing a scaling parameter for each amino acid in order to 'best fit' the codon usage of our reading frames to the reported codon usage of the corresponding amino acid in the 71 representative organisms. The minimized sum of the squared differences (equation 1) was used as a measure of the similarity of codon usage for all tested amino acids:

$$\varepsilon_A = \sum_{i=1}^{n} (f_{i,A} - C_A * g_{i,A})^2 \quad (1)$$

in which $f_{i,A}$ represents the percent usage of the $i^{th}$ codon of amino acid A in the reading frame being tested, $g_{i,A}$ is the percent usage of the $i^{th}$ codon of amino acid A in the organism being tested against, $C_A$ is the optimization parameter used as a fitting factor for amino acid A, and n is the number of codons existing for amino acid A. These individual amino acid measures ($\in$) were summed (equation 2) to produce an overall measure of fit (F) for the analyzed reading frame:

$$F = \sum_{1}^{m} \varepsilon_A \quad (2)$$

in which m is the number of different codons used for amino acid A.

The use of a single optimization parameter ($C_A$) per amino acid preserved the pairwise codon ratios existing within each amino acid of the organism being tested while simultaneously adjusting for any frequency of use differences that an amino acid might have in our reading frame versus its average usage in a given, much larger genome. The amino acids methionine and tryptophan, which use only one codon each, always generate a zero value for $\in$ and thus do not have an effect in this analysis.

Availability of nucleotide sequences. The novel (nonrd) nucleotide sequences identified herein will be made available on a website.

PCR-based Gene Distribution Studies. Primer pairs designed to obtain internal sequence data for each *H. influenzae* clone were also used for PCR-based distribution studies in which genomic DNA isolated from each clinical strain and from the laboratory reference strain Rd were used as templates to determine the number of clinical strains that possessed each nonRd sequence. A positive control reaction for each genomic template DNA was also performed using primers specific for the *H. influenzae* glyceraldehyde-3-phosphate dehydrogenase (GAPDH) gene (Table 1). PCR was performed using the Eppendorf MasterTaq Kit (Brinlanan Instruments, Inc., Westbury, N.Y.) in a 25 μl reaction mixture. Standard reactions included 0.6 units of Taq DNA polymerase, 50 ng of template DNA, 20 pmol of each primer, 1.5 mM MgCl$_2$, and 0.2 mM dNTPs. Reactions were carried out in Perkin Elmer 9600 thermal cyclers and included an initial 10-minute denaturation step at 95° C. The amplification cycle consisted of 30 s at 94° C., 1 min at 55° C., and 1 min at 72° C. for 35 cycles. This was followed by a final extension step of 7 min at 72° C. and then a 4° C. hold. Reactions were analyzed on 1.7% agarose gels that were stained with ethidium bromide.

Redundancy of the pooled genomic library. The library of pooled genomic DNA from the ten clinical *H. influenzae* strains was comprised of 76,800 clones. Accounting for the approximately 25% of clones having oligonucleotide inserts or low viability (data not shown), the functional library contained approximately 57,000 clones. The average insert size of the library clones was 1.5 kb, resulting in a library that consisted of approximately $8.55 \times 10^7$ bp of DNA from the 10 clinical strains. Since the genome size of *H. influenzae* is approximately 1.83 Mb (Fleischmann, R. D., M. D. Adams, O. White, R. A. Clayton, E. F. Kirkness, A. R. Kerlavage, C. J. Bult, J.-F. Tomb, B. A. Dougherty, J. M. Merrick, K. McKenney, G. Sutton, W. FitzHugh, C. Fields, J. D. Gocayne, J. Scott, R. Shirley, L.-I. Liu, A. Glodek, J. M. Kelley, J. F. Weidman, C. A. Phillips, T. Spriggs, E. Hedblom, M. D. Cotton, T. R. Utterback, M. C. Hanna, D. T. Nguyen, D. M. Saudek, R. C. Brandon, L. D. Fine, J. L. Fritchman, J. L. Fuhrmann, N. S. M. Geoghagen, C. L. Gnehm, L. A. McDonald, K. V. Small, C. M. Fraser, H. O. Smith, and J. C. Venter. 1995. Whole genome random sequencing and assembly of *Haemophilus influenzae* Rd. Science 269:496–512, incorporated by reference herein), the redundant library provided a 4.6×coverage of each of the 10 genomes.

Comparison of DNA sequences to the *H. influenzae* Rd genome. The nucleotide sequences of 771 randomly chosen clones from the pooled *H. influenzae* library were analyzed. This set of sequenced clones represented 1.35% of the functional library. The clones were sequenced with both forward and reverse primers, with an average read length of 650 bases obtained at each end for each clone. This provided us with approximately 87% of the complete sequence for the average-sized (1.5 kb) clone. The sequences obtained were compared to that of the published sequence of the *H. influenzae* Rd reference genome to identify those novel sequences present in the set of clinical isolates but absent in this less virulent laboratory reference strain.

Clones displaying at least 350 bp of contiguous homology to Rd at each end were classified as Rd-like. To ensure that there were no large deletions or insertions in these sequences, the size of each clone (determined by restriction endonuclease analysis) was compared to the size of the corresponding region on the Rd genome. Using this method, 699 (90.7%) of the clones as Rd-like sequences were classified.

However, it is possible that this value is deceptively high, since the unsequenced regions of many of the clones could contain subtle, unidentified deviations from the respective Rd sequences that were not detected by electrophoretic sizing of the insert. In fact, possible small insertions and deletions in several of the Rd-like clones were already detected, and the detailed analysis and verification of these changes are in progress and part of future studies.

Identification of novel (non rd) DNA sequences. BLASTn analysis of the initial sequences obtained for 72 clones (9.3% of the total number of clones analyzed) indicated that these clones either varied significantly or were absent entirely from the Rd genome. Complete double-stranded sequence was then obtained, and a consensus sequence was assembled, for each of these clones. The consensus sequences of these 72 clones were then compared to each other to determine if any sequence occurred in more than one clone. Each set of overlapping consensus sequences were compiled into a contig sequence, resulting in the formation of nine contigs using the sequences of 21 clones. These nine contig sequences, in addition to the consensus sequences of the 51 remaining clones, were used to perform additional nucleotide (BLASTn) and amino acid (BLASTx) homology searches. Of these 60 sequences, 40 displayed no nucleotide-level homology to the Rd genome. The remaining 20 sequences contained varying lengths of homologous regions to Rd in addition to significant ($\geq 200$ bp) regions not present in Rd.

Distribution of cloned Rd-like sequences on the Rd genome. FIG. 1 shows the regions of the Rd genome represented in the cloned sequences. Sequences from the entire Rd chromosome were distributed evenly in the set of clones, suggesting that the clones did not overrepresent a single pathogenicity island per se. The equal distribution of randomly selected clones along the *H. influenzae* Rd chromosome indicated that the redundant pooled genomic library was not degraded and was unbiased in its coverage of the ten clinical isolates. Additionally, the 20 sequences that exhibited varying degrees of Rd homology were also distributed evenly throughout the Rd chromosome.

Distribution of novel sequences among the ten OM isolates. Primer pairs (Table 1) flanking nonRd sequences were used in PCR-based studies to detect the presence or absence of the novel nucleotide sequences in the genomes of the 10 *H. influenzae* clinical strains and also in Rd. Each primer pair was tested initially using plasmid DNA from the respective clone as the template. The primer pairs that supported amplification using the corresponding plasmid clones were further used in the genomic distribution study. The presence of a PCR product at the predicted molecular weight following agarose gel electrophoresis was taken as evidence that the novel sequence was present in the genome of the clinical isolate.

Data for these genomic distribution studies were summarized in Table 3. If the distribution patterns were the same for clones that formed a contig sequence, distribution pattern was reported only once. In a few cases, the individual distribution patterns for overlapping clones were reported because each provided unique information. The mean distribution of the unique sequences was 8.48±2.55 strains. The mode and the median were both equal to 10. None of the ten clinical strains harbored the same set of unique sequences. Interestingly, the distribution of the nonRd sequences in the encapsulated strain AA did not appear to be substantially different from those of the nine NTHi isolates.

Occurrence of tandem oligonucleotide repeat sequences. The novel sequences were searched for tandem repeats of oligonucleotides ranging in length from two to 17 bases. Variable-number-of-tandem-repeat regions (VNTRs) in *H. influenzae* and other pathogenic bacteria are associated with phenotypic switching and virulence (Hood, D. W., M. E. Deadman, M. P. Jennings, M. Bisercic, R. D. Fleischmann, J. C. Venter, and E. R. Moxon. 1996. DNA repeats identify novel virulence genes in *Haemophilus influenzae*. Proc. Natl. Acad. Sci USA. 93:11121–11125; van Belkum, A., S. Scherer, W. van Leeuwen, D. Willemse, L. van Alphen, and H. Verbrugh. 1997. Variable number of tandem repeats in clinical strains of *Haemophilus influenzae*. Infect. Immun. 65:5017–5027, both of which are incorporated by reference herein). Five VNTRs were identified, each in a different clone: a mononucleotide repeat (121_L20); two tetranucleotide repeats (151_O4 and Hb_contig); a pentanucleotide repeat (179_D14); and an 11-mer repeat (162_D23). The mononucleotide repeat in 121_L20, which had a G+C content of only 32%, consisted of 12 G-residues. The remaining VNTR sequences, and their potential functions, are presented below in the context of the respective clones.

Occurrence of USSs in unique clones. Each of the nonRd sequences were also searched for the presence of the *Haemophilus* and *Neisseria* USSs. Bacteria belonging to both of these genera are naturally competent and preferentially take up DNA containing their respective USS. The *Haemophilus* uptake sequence (hUSS) consists of a conserved 9-bp core sequence contained within a 29-bp sequence 5'-aAAGTGCGGTnRWWWWWnnnnnnRWWWWW-3' (Danner, D. B., R. A. Deich, K. L. Sisco, H. O. Smith. 1980. An eleven-base-pair sequence determines the specificity of DNA uptake in *Haemophilus* transformation. Gene 11:311–318; Goodgal, S. H., and M. A. Mitchell. 1990. Sequence and uptake specificity of cloned sonicated fragments of *Haemophilus influenzae* DNA. J. Bacteriol. 172: 5924–5928; Smith, H. O., J.-F. Tomb, B. A. Dougherty, R. D. Fleischmann, and J. C. Venter. 1995. Frequency and distribution of DNA uptake signal sequences in the *Haemophilus influenze* Rd genome. Science 269:538–540, all of which are incorporated by reference herein). The neisserial sequence (nUSS) is the 10-bp sequence 5'-GCCGTCTGAA-3' (Elkins, C., C. E. Thomas, H. S. Seifert, and P. F. Sparling. 1991. Species-specific uptake of DNA by gonococci is mediated by a 10-base-pair sequence. J. Bacteriol. 173: 3911–3913; Goodman, S. D., and J. J. Scocca. 1988. Identification and arrangement of the DNA sequence recognized in specific transformation of *Neisseria gonorrhoeae*. Proc. Natl. Acad. Sci. U.S.A. 85:6982–6986, both of which are incorporated by reference herein). 32 hUSSs and 2 nUSSs distributed among 28 genomic clones (Table 4) were identified. No cloned fragment contained both an hUSS and an nUSS, although several contained more than one hUSS.

Nucleotide homologies displayed by nonRd sequences. BLASTn analysis of the 60 nonRd sequences listed in Table 4 revealed that only 18 had strong homology to a known nucleotide sequence. 14 of these 18 were homologous to DNA from pathogenic strains of *H. influenzae*. The FPG_contig and 97_H3 showed strong nucleotide homology (97% and 81%, respectively) to DNA from the closely related pathogenic bacterium *Pasteurella multocida*. Clone 100_E23 was 99% homologous to *H. influenzae* phage HP2, and 179_D14 was 88% homologous to DNA from the plant pathogen *Ralstonia solanacearum*.

Three-frame, forward and reverse, BLASTx analysis were then performed to determine if the conceptual protein translations of the nonRd sequences demonstrated homology to any known proteins. Given that random clones ordinarily code for only partial open reading frames (ORFs), the BLASTx analysis frequently involved the comparison of partial protein sequences to the full-length sequences in the protein databases. To aid in the interpretation of the reported homologies, and to avoid the misconception that a full-length ORF was always analyzed, each translated sequence as a region of homology (ROH) was defined. An ROH may have contained stop codons or frameshifts that were trangressed in favor of continuing a strong homology. Multiple ROHs for the majority of the clones were analyzed. Table 4 summarizes the data obtained from the extensive sequence analysis and homology searches using the nonRd sequences. For each ROH, its length (in amino acids) along with the length of its primary protein homolog was reported. Homologies are described in more detail below.

Homologies to *H. influenzae* virulence factors. 20% of the nonRd clones that were analyzed exhibited homology (both nucleotide and amino acid) to *H. influenzae* virulence factors. One fourth of this subset was homologous to the *H. influenzae* fimbrial gene cluster (hij), which is missing in Rd (van Ham, S. M., L. van Alphen, F. R. Mooi, and J. P. M. van Putten. 1994. The fimbrial gene cluster of *Haemophilus influenzae* type b. Mol. Microbiol. 6:277–282, incorporated by reference herein). Three clones were homologous to two major adherence proteins of nontypeable *H. influenzae* isolates, the high-molecular-weight (HMW) surface-exposed proteins HMW1 and HMW2 (Barenkamp, S. J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302–1313, incorporated by reference herein).

Clone 135_I10 was homologous to the putative virulence-associated autotransporter protein, Las, from *H. influenzae* biogroup aegyptius. Autotransporters are outer membrane proteins (OMPs) involved in the establishment and dissemination of infection and include *H. influenzae* Lav, *N. meningitidis* VapA and *Bordetella pertussis* PerT (Davis, J., A. L. Smith, W. R. Hughes, and M. Golomb. 2001. Evolution of an autotransporter: domain shuffling and lateral transfer from pathogenic *Haemophilus* to *Neisseria*. J. Bacteriol. 183:4686–4635, incorporated by reference herein). lav is a mobile contingency gene located within a pair of hUSSs (J. Davis, et al., 2001), and 135_I10 did contain an hUSS, but it occurred within the putative autotransporter ORF.

Two clones (9_E14 and 13_D9) that were homologous to the tryptophanase genes tnaA and tnaB from Hib strain Eagan (Martin, K., G. Morlin, A. Smith, A. Nordyke, A. Eisenstark, and M. Golomb. 1998. The tryptophanase gene cluster of *Haemophilus influenzae* type b: evidence for horizontal gene transfer. J. Bacteriol. 180:107–118, incorporated by reference herein) were compiled to form the Tna_contig sequence. The ability to catabolize tryptophan is strongly associated with virulence, and the tna cluster appears to act as a pathogenicity island (K. Martin et al., 1998). Genomic DNA from all 10 of the OM isolates supported PCR with a tnaB-specific primer set (see 9_E14 in Table 3). However, results generated with a primer pair including a tnaA-specific primer implied that only seven of the clinical strains had the tryptophanase structural gene tnaA (see 13_D9 in Table 3).

Clone 83_M12 contained the entire lex2A ORF and the 5' region of lex2B from Hib strain DL42. The Lex2B_contig (formed from clones 47_C18 and 93_M17) contained the 3' end of lex2B and did not overlap with 83_M12. The lex2AB genes are involved in the variable expression of lipooligosaccharide (LOS) epitopes, which results in alterations in virulence (Cope, L. D., R. Yogev, J. Mertsola, J. L. Latimer, M. S. Hanson, G. H. McCracken, Jr. and E. J. Hansen. 1991. Molecular cloning of a gene involved in lipooligosaccharide biosynthesis and virulence expression by *Haemophilus influenzae* type B. Mol. Microbiol. 5:1113–1124; Foxwell, A. R., J. M. Kyd, and A. W. Cripps. 1998. Nontypeable *Haemophilus influenzae*: pathogenesis and prevention. Microbiol. Mol. Biol. Rev. 62:294–308; Jarosik, G. P., and E. J. Hansen. 1994. Identification of a new locus involved in expression of *Haemophilus influenzae* type b lipooligosaccharide. Infect. Immun. 62:4861–4867, all of which are incorporated by reference herein). The lex2A allele contained only three repeating units of the tetranucleotide GCAA, which occurs 18 times in the 5' region of lex2A in strain DL42 (Jarosik et al., 1994). The sequence 3upstream of lex2A in 83_M12 was homologous to *H. influenzae* Rd purL. This nucleotide homology ended abruptly where the homology to the lex2AB locus began. A 15-bp sequence (5'-CAGATTTTCACTGTG-3') was identified that is present both downstream of the Rd purL and upstream of the lex2A in strain DL42 and which probably facilitated the insertion of the lex2 genes. A hUSS 10 bp upstream of this 15-bp sequence was also identified, indicating that this region of DNA would be preferentially taken up via transformation into *H. influenzae*.

Homologies to *H. influenzae* hemoglobin-binding proteins. The sequences of three overlapping clones (101_K4, 131_L20, and 153_C10) to form one Hb_contig sequence of 4,518 bp were complied, which provided a more comprehensive view of this locus. Over half (>2,350 bp) of this contig sequence was novel with respect to known sequences in the public databases, although each end was highly homologous (>90%) to hgpA from Hib strain HI689 (Jin, H., Z. Ren, J. M. Pozsgay, C. Elkins, P. W. Whitby, D. J. Morton, and T. L. Stull. 1996. Cloning of a DNA fragment encoding a heme-repressible hemoglobin-binding outer membrane protein from *Haemophilus influenzae*. Infect. Immun. 64:3134–3141; Jin, H., Z. Ren, P. W. Whitby, D. J. Morton, and T. L. Stull. 1999. Characterization of hgpA, a gene encoding a hemoglobin/hemoglobin-haptoglobin-binding protein of *Haemophilus influenzae*. Microbiology 145:905–914, both of which are incorporated by reference herein). hgpA encodes a protein that binds both hemoglobin and the hemoglobin-haptoglobin complex (Jin et al., 1999). BLASTx analysis of our contig revealed a complete ORF with comparable homologies to a number of *H. influenzae* hemoglobin-binding proteins, including the gene products of hgpA, hgpB, hgpC, hhuA.

Like many of these genes that encode OMPs involved in hemoglobin binding, the putative ORF contained a series of CCAA nucleotide repeats near the N-terminus (Fleischmann, et al., 1995; Hood et al., 1996; Jin et al., 1999; Maciver, I., J. L. Latimer, H. H. Liem, U. Muller-Eberhard, Z. Hrkal, and E. J. Hansen. 1996. Identification of an outer membrane protein involved in utilization of hemoglobin-haptoglobin complexes by nontypeable *Haemophilus influenzae*. Infect. Immun. 64:3703–3712, all of which are incorporated by reference herein). Ren et al. (Ren et al., 1999) have shown that changes in the number of CCAA repeats in hgpA mediate phase variable expression. Another characteristic that ORF shares with hgpA is the presence of a direct repeat, with unknown function, upstream of the putative start codon (Jin et al., 1996).

The sequence downstream of the cloned hgpA-like ORF suggested that this locus is located in the same region of its respective genome as hgpA in strain HI689. The HI689 hgpA is located upstream of pepE, in place of ORFs HI0588, HI0589, HI0590, HI0591 and HI0592, which are upstream of pepE on the Rd genome (Jin et al., 1999). Approximately 500 bp downstream of our putative hemoglobin-binding ORF was the start of a second, incomplete ORF that displayed 98% identity to the corresponding region of the Rd pepE.

Clone 32_B2 also displayed some homology to *H. influenzae* hemoglobin-binding proteins. Of the 1,199 bp in this clone, only an internal region of 332 bp displayed significant nucleotide-level homology (91%) to any sequences in the public databases. This homology was to the 3' end of hhuA from the nontypeable *H. influenzae* strain TN106 (Maciver et al., 1996). In addition, the theoretical translation of 32_B2 was 57% identical to the final 191 amino acids of the hemoglobin-haptoglobin binding protein HhuA (Table 4). These results suggested that 32_B2 contained the 3' end of an incomplete ORF, which is either a newly identified allele of hhuA or which encodes another homolog to the group of *H. influenzae* proteins involved in the uptake of heme.

Homology to *Pasteurella multocida* formamidopyrimidine DNA glycosylase (FPG). The entire 1.66 kb Fpg_contig sequence (compiled from clones 112_A12 and 134_O6) was 97% homologous to the *P. multocida* fpg, which encodes formamidopyrimidine-DNA glycosylase. Only three dispersed regions (≦70 nt each) were homologous to the Rd genome, despite the fact that Rd has an fpg gene. The presence of two hUSSs, one within the *P. multocida* fpg and the other downstream, indicated that this *Pasteurella* DNA had probably been taken up and incorporated into *H. influenzae* by way of transformation. Eight of our isolates were shown to harbor this *P. multocida* fpg locus (Table 3).

Homology to the *N. meningitidis* YhbX/YhjW/YijP/YjdB family protein. The predicted amino acid sequence for the novel sequence in clone 151_O4 exhibited greatest homology (47% identical, 68% similar; Table 4) to the hypothetical YhbX/YhjW/YijP/YjdB family protein in *Neisseria meningitidis* (Parkhill J., M. Achtman M, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehead, B. G. Spratt, B. G. Barrell. 2000. Complete DNA sequence of a serogroup A strain of *Neisseria meningitidis* Z2491. Nature 404:502–506; 60, incorporated by reference herein). This meningococcal protein is named for its homology to a group of probable membrane-associated proteins originally identified in *E. coli*. Most interesting is the *E. coli* YijP, which is involved in the penetration of the blood-brain barrier and has been demonstrated to contribute to the pathogenesis of *E. coli* meningitis (Wang, Y., S.-H. Huang, C. A. Wass, M. F. Stins, and K. S. Kim. 1999. The gene locus yijP contributes to *Escherichia coli* K1 invasion of brain microvascular endothelial cells. Infect. Immnun. 67:4751–4756, incorporated by reference herein).

Genomic PCR distribution studies revealed that all ten otitis media isolates contain the novel sequence cloned in 151_O4 (Table 3). This widespread distribution may be due to the presence of an hUSS 375 bp upstream of the predicted ORF. Also noteworthy is a tract of six copies of the tetranucleotide TTTG within the first 150 nt of the putative ORF. Tetranucleotide repeats in the 5' ends of *H. influenzae* reading frames have been associated with slipped-strand mispairing, resulting in frame shifts that lead to phase-variable expression of a number of surface protein genes (Davis, J., A. L. Smith, W. R. Hughes, and M. Golomb. 2001. Evolution of an autotransporter: domain shuffling and lateral transfer from pathogenic *Haemophilus* to *Neisseria*. J. Bacteriol. 183:4686–4635; Hood, D. W., M. E. Deadman, M. P. Jennings, M. Bisercic, R. D. Fleischmann, J. C. Venter, and E. R. Moxon. 1996. DNA repeats identify novel virulence genes in *Haemophilus influenzae*. Proc. Natl. Acad. Sci USA. 93:11121–11125; Ren, Z., H. Jin, P. W. Whitby, D. J. Morton, and T. L. Stull. 1999. Role of CCAA nucleotide repeats in regulation of hemoglobin and hemoglobin-haptoglobin binding protein genes of *Haemophilus influenzae*. J. Bacteriol. 181:5865–5870, all of which are incorporated by reference herein).

Clonal similarity to a *Shigella flexneri* pathogenicity island. The 1,802-bp *H. influenzae* fragment cloned in 125_L2 is a novel polynucleotide that was detected in 9 of the 10 pathogenic *Haemophilus influenzae* isolates (Table 3). Sequence similarity searches revealed two short regions (approximately 75 bp each) that displayed nucleotide homology (83%) to the *Shigella* resistance locus (SRL) pathogenicity island (PAI) of *S. flexneri* type 2a. The 66,257-bp SRL PAI carries genes for antibiotic resistance, iron uptake, and at least 22 prophage-related ORFs (Luck, S. N., S. A. Turner, K. Rajakumar, H. Sakellaris, and B. Adler. 2001. Ferric dicitrate transport system (Fec) of *Shigella flexneri* 2a YSH6000 is encoded on a novel pathogenicity island carrying multiple antibiotic resistance genes. Infect.

Immun. 69:6012–6021, incorporated by reference herein). The conceptual translation of the 125_L2 sequence and subsequent homology search revealed 3 open reading frames (one complete, two incomplete). All three inferred protein products of this clone were homologous to the proteins encoded by ORFs 7, 8 and 9 of the SRL PAI (Luck, S. N., S. A. Turner, K. Rajakumar, H. Sakellaris, and B. Adler. 2001. Ferric dicitrate transport system (Fec) of *Shigella flexneri* 2a YSH6000 is encoded on a novel pathogenicity island carrying multiple antibiotic resistance genes. Infect. Immun. 69:6012–6021, incorporated by reference herein). These *Shigella* homologs included a probable LysR-like transcriptional regulator (ORF 7; 64% identical, 73% similar), an unknown protein (ORF 8; 58%, 78%), and a putative anaerobic decarboxylate transporter (ORF 9; 54% identical, 64% similar).

Presence of a tetratricopeptide repeat (TPR) protein. The nucleotide sequence of clone 167_A16, which was 2,597 nt in length, displayed only two, short regions of 55 and 60 nt with homology (96% and 90%, respectively) to Rd. The remaining sequence displayed no significant homologies to any known DNA sequence. The proposed amino acid sequence suggested that this clone encodes at least one protein with a tetratricopeptide repeat (TPR) motif The tetratricopeptide repeat, which has been identified in a wide variety of proteins, is a structural motif that mediates protein-protein interactions (Blatch, G. L., and M. Lassle. 1999. The tetratricopeptide repeat: a structural motif mediating protein-protein interactions. Bioessays 21:932–939, incorporated by reference herein). The proteins with the highest homologies to our hypothetical TPR protein (167_A16 ROH2, Table 4) are almost exclusively from bacterial pathogens. Many of these homologs are, themselves, hypothetical proteins with unknown functions, including the *Haemophilus somnus* protein displaying the greatest homology (42% identical; 60% similar). A few homologs, however, have assigned functions that lead us to speculate on the potential significance of this protein in *H. influenzae*. Included in these are the *Legionella pneumophila* enhanced entry protein (enhC gene product), which is involved in entry into host cells, and a *Helicobacter pylori* antigen (protein H) that granted significant protection against *H. pylori* challenge in a mouse model system (Cirillo, S. L., G., J. Lum, and J. D. Cirillo. 2000. Identification of novel loci involved in entry by *Legionella pneumophila*. Microbiology 146:1345–1359; Hocking, D., E. Webb, F. Radcliff, L. Rothel, S. Taylor, G. Pinczower, C. Kapouleas, H. Braley, A. Lee, and C. Doidge. 1999. Isolation of recombinant protective *Helicobacter pylori* antigens. Infect. Immun. 67:4713–4719, both of which are incorporated by reference herein).

Another region (ROH1) was analyzed, downstream of the putative ORF for the TPR protein, that appeared to have a very weakly conserved TPR motif. Its primary homolog was a conserved hypothetical *H. pylori* protein. Finally, the conceptual translation of a third putative coding region (ROH3) showed no evidence of a TPR motif and had greatest homology to a *Listeria monocytogenes* protein that is similar to the putative integral membrane protein, ComEC, which is required for DNA uptake in bacteria (Glaser, P., L. Frangeul, C. Buchrieser, C. Rusniok, A. Amend, F. Baquero, P. Berche, H. Bloecker, P. Brandt, T. Chakraborty, A. Charbit, F. Chetouani, E. Couve, A. de Daruvar, P. Dehoux, E. Domann, G. Dominguez-Bernal, E. Duchaud, L. Durant, O. Dussurget, K. D. Entian, H. Fsihi, F. G. Portillo, P. Garrido, L. Gautier, W. Goebel, N. Gomez-Lopez, T. Hain, J. Hauf, D. Jackson, L. M. Jones, U. Kaerst, J. Kreft, M. Kuhn, F. Kunst, G. Kurapkat, E. Madueno, A. Maitournam, J. M. Vicente, E. Ng, H. Nedjari, G. Nordsiek, S. Novella, B. de Pablos, J. C. Perez-Diaz, R. Purcell, B. Remmel, M. Rose, T. Schlueter, N. Simoes, A. Tierrez, J. A. Vazquez-Boland, H. Voss, J. Wehland, and P. Cossart. 2001. Comparative genomics of Listenra species. Science 294: 849–852, incorporated by reference herein).

Homology to bacterial conjugation proteins. The DNA sequence of 179_D14 was highly homologous (88%) to the trbB gene of the phytopathogen *Raistonia solanacearum*, and its deduced amino acid sequence is 91% identical to the *R. solanacearum* probable conjugal transfer protein TrbB (Salanoubat, M., S. Genin, F. Artiguenave, J. Gouzy, S. Mangenot, M. Arlat, A. Billault, P. Brottier, J. C. Camus, L. Cattolico, M. Chandler, N. Choisne, C. Claudel-Renard, S. Cunnac, N. Demange, C. Gaspin, M. Lavie, A. Moisan, C. Robert, W. Saurin, T. Schiex, P. Siguier, P. Thebault, M. Whalen, P. Wincker, M. Levy, J. Weissenbach, and C. A. Boucher. 2002. Genome sequence of the plant pathogen Ralstonia solanacearum. Nature 415:497–502, incorporated by reference herein). TrbB belongs to an extensive superfamily of proteins involved in the formation of surface-associated protein complexes that mediate a number of diverse processes such as pilus biosynthesis, DNA transport, and the secretion of virulence factors (Hobbs, M., and J. S. Mattick. 1993. Common components in the assembly of type 4 fimbriae, DNA transfer systems, filamentous phage and protein-secretion apparatus: a general system for the formation of surface-associated protein complexes. Mol. Microbiol. 10:233–243; Whitchurch, C. B., M. Hobbs, S. P. Livingston, V. Krishnapillai, and J. S. Mattick. 1990. Characterization of a *Pseudomonas aeruginosa* twitching motility gene and evidence for a specialized protein export system widespread in eubacteria. Gene 101:33–44, both of which are incorporated by reference herein). This superfamily encompasses both archeal and bacterial proteins and includes the subfamily of type IV NTPases to which TrbB proteins belong (Planet, P. J., S. C. Kachlany, R. DeSalle, and D. H. Figurski. 2001. Phylogeny of genes for secretion NTPases: identification of the widespread tadA family and development of a diagnostic key for gene classification. Proc. Natl. Acad. Sci USA 98:2502–2508, incorporated by reference herein). A pentanucleotide repeat (CCGGC) in 179_D14 was also identified that repeats three times and is located within the putative ORF. The strong DNA homology of this clone to *R. solanacearum*, and its extraordinarily high G+C (68%) content compared to that of *Haemophilus* DNA (38%), suggests that this DNA was recently acquired by *H. influenzae*.

Presence of an 11-mer repeat. An 11-mer (5'-GGAAT-TATTTG-3') in 162_D23 was detected that repeats slightly over seven times. The *H. influenzae* DNA fragment cloned in 162_D23 was only 462 bp, and the first 130 bp represented the 3' end of the Rd holA. Downstream of the holA homology was a short (58 bp) region of homology (82%) to *Oryza sativa* genomic DNA. However, none of the DNA downstream of the probable holA had significant amino acid-level homology to any known proteins. The 11-mer repeat begins approximately 180 nt downstream of holA and spans the region of homology to *O. sativa*. If translated, this repeat results in the appearance of the amino acid sequence LGIIWELFGNYLGIIWELFG in all three positive reading frames. The slightly longer translated sequence NYLGII-WELFGNYLGIIWFLFG appears in two of the three positive reading frames. Interestingly, the Rd genome contains one 15-mer repeat, two 12-mer repeats, and a 9-mer repeating unit, none of which is repeated more that four times.

Codon usage of nonRd sequences. The codon usage of each of the analyzed ROHs was compared to the codon usage of 71 organisms (Table 2) using a least squares fitting procedure. Six of the 71 organisms were *Haemophilus* types: three *Haemophilus influenzae* strains, two *Haemophilus influenzae* phage (HP 1, HP2), and *Haemophilus ducreyi*. It was shown (J. Gladitz et al., manuscript in preparation) that the least squares fitting procedure used suffers an exponential loss in its power to minimize ∈ (measure of fit) with decreasing sequence lengths. In that study, it was found that 50% of the analyzed *H. influenzae* Rd genes that were shorter than 160 codons had codon usage that best fit a non*Haemophilus* organism, yet only 10% of the *H. influenzae* Rd genes greater than 0.200 codons best fit a non*Haemophilus* organism. Consequently, only those nonRd ROHs listed in Table 4 that were 160 codons or longer were analyzed for codon usage in this study.

A subset of 52 of the ROHs listed in Table 4 qualified for the codon study. The actual lengths of the sequences analyzed were, in some cases, longer than their regions of homology (ROHs) listed in Table 4; this occurred when the corresponding amino acid sequence continued without any stop codons. In some cases, the codon populations for adjacent ROHs were combined in an attempt to provide greater statistical relevance. This approach was usually applied when the protein homologies suggested that the ROHs originated from the same organism. In a few cases, an ROH shorter than 160 codons was combined with an adjacent ROH for analysis, regardless of their protein-level homologies; although ROHs exhibiting phage homology were not combined with ROHs without phage homology.

The organism that provided the best overall measure of fit (i.e., lowest ∈-value) for each analyzed ROH is listed in Table 5. The lowest ∈-value amongst the *Haemophilus* grouping is always provided, even for those cases when the best fit was to a non *Haemophilus* organism. When the lowest ∈-value was to one of the two *H. influenzae* phage (HP1 and HP2), then the lowest ∈-value amongst the *Haemophilus* species was also included.

The hifC (4_E21 ROH1) and hifD (4_E21 ROH2 and 152_N2 ROH1) alleles identified were found to have high G+C contents (45%, 46%, and 48%, respectively). The codon usage of the hifC allele (4_E21 ROH1) showed greater similarity to the *Haemophilus*-specific phage HP2 than to the *Haemophilus* bacterial strains, though its codon usage patterns were shown to be well-adapted to *Haemophilus* (Table 5). For comparison, the hifC allele from Hib strain Eagan (Watson, W. J., J. R. Gilsdorf, M. A. Tucci, K. W. McCrea, L. J. Forney, and C. F. Marrs. 1994. Identification of a gene essential for piliation in *Haemophilus influenzae* type b with homology to the pilus assembly platform genes of gram-negative bacteria. Infect. Immun. 62:468–475, incorporated by reference herein) was analyzed, which has a G+C content of 44%, and determined that its codon usage is also closest to that of phage HP2, with a very low ∈-value of 13.45.

The hifD (4_E21 ROH2 and 152_N2 ROH1) alleles produced high ∈-values, with little similarity in codon usage to any of the sample organisms (Table 5). To determine if this atypical codon usage were unique to the hifD alleles, the hifD gene was analyzed from Hib strain Eagan for codon usage. This hifD allele has a 47% G+C content (40) and, likewise, displayed little codon-usage similarity to any sample organism. The best-fitting organism for the Eagan hifD was phage HP2 (∈-value=54.21). Taken together, these results indicated that *H. influenzae* maintains a deviant codon usage for hifD.

Unlike hifC and hifD, the fimbrial adhesin gene, hifE, does have a G+C content typical of *Haemophilus*. Two ROHs (133_D6 and 152_N2 ROH2) were identified as hijE alleles, which have the highest amino-acid level homologies to the *H. influenzae* biogroup aegyptius protein (Table 4). The codon populations for these two ROHs were combined for analysis of these two hijE alleles since each was too short to qualify for individual analysis (Table 4). This was justified because these ROHs represented different regions of the hifE locus, with no overlapping sequence. The analysis revealed *H. influenzae* biogroup aegyptius as the best-fit organism (∈-value=17.74). Analysis of the type b Eagan hifE quantitatively reproduced these results, as *H. influenzae* biogroup aegyptius was indeed the best-fitting organism with an ∈-value of 9.15.

A hypothetical protein was identified that is highly homologous to a putative glucosidase in *Yersinia pestis*. This clone (43_I10) exhibited codon usage patterns well-adapted to *Haemophilus* (∈-value=14.0) and not to *Yersinia* (∈-value=115.45) (Table 5). The G+C content (36%) was also *Haemophilus*-like and very different from that of *Yersinia* (49%) (Table 2). These two pieces of evidence suggest that the glucosidase in *Yersinia* and the 43_I10 glucosidase homolog which was identified in *Haemophilus* shared a common ancestor and have been evolving separately under the distinct selective pressures of their various host organisms for an extended time. It appears, thus, that 43_I10 has been a longtime member of the NTHi supra-genome as opposed to having been recently acquired by horizontal exchange.

The primary homologs from all three gene products in the clone 125_L2 were identified as proteins encoded by a pathogenicity island from *Shigella flexneri* 2a. It thus appears that they may have transferred into *Haemophilus* as a group, possibly from *Shigella* directly. When these three ROHs were analyzed collectively for codon usage, their resulting ∈-value for *S. flexneri* 2a was quite poor (110.72), suggesting that they have been evolving separately from those genes in *Shigella* for an extended time. In addition, the G+C contents for all three ROHs (Table 4) were very different from that of *S. flexneri* 2a (48%). The G+C content was in fact *Haemophilus*-like; however, unlike the case of 43_I10 where the codon usage supported the long-time presence of the sequence in *Haemophilus*, in this case it did not. The closest fitting organism for this clone was enterobacteria phage T4.

Sixteen of the sequences listed in Table 5 had been shown by BLASTx analysis to encode homologs of phage proteins. Of these, 10 displayed codon usage patterns that revealed *Haemophilus* phage to be the best-fitting organism. Two additional ROHs, 32_F13 ROH1 and 126_N4 ROH2, also have codon usage patterns best fitting that of *Haemophilus* phage; however, their primary BLASTx homologies were not to phage proteins. Although, in the case of 32_F13 ROH1, there were large regions of homology throughout the ROH to proteins from prophage CP-933C and the *Haemophilus* phage φ-R73.

Clones 124_K4 and 157_C17 were identified by BLASTx analysis to encode homologs (61% identical and 66% similar, respectively) of *Vibrio cholera* proteins; and, *V. cholerae* was selected as the best-fitting organism for these two clones (Table 5). Similarly, an excellent example of an ROH that exhibited strong codon-usage similarity to one of the non-*Haemophilus* organisms in the study, while at the same time having an extremely high ∈-value for *Haemophilus*, is 179_D14. This clone has a 68% G+C content and likely signifies a recent acquisition by horizontal transfer. The codon usage of this ROH was most similar to that of the G+C-rich bacterium *P. aeruginosa* (∈-value=19.65). The 179_D14 sequence is 88% homologous at the nucleotide level to the trbB gene of *Ralstonia solanacearum* (Table 4), a bacterium which is closely related to *P. aeruginosa*. *P. aeruginosa*, itself, has limited nucleotide homology to 179_D14 (42 nt with 88% identity).

The availability of complete bacterial genomic sequences over the last several years has revealed a strikingly high degree of genomic diversity among bacteria of the same species, particularly among bacterial pathogens. Substantial differences in genome size and organization have been identified, in addition to a relationship between metabolic diversity and genome size (Dobrindt, U., and J. Hacker. 2001. Whole genome plasticity in pathogenic bacteria. Curr. Opin. Microbiol. 5:550–557, incorporated by reference herein). From these studies it is becoming apparent that bacterial pathogens share an apportioned population-based genome or supra-genome, and that individual strains each contain only a subset of the contingency genes present among the entire population (Dobrindt, U., and J. Hacker. 2001. Whole genome plasticity in pathogenic bacteria. Curr. Opin. Microbiol. 5:550–557; Hacker, J., and E. Carniel. 2001. Ecological fitness, genomic islands and bacterial pathogenicity: a Darwinian view of the evolution of microbes. EMBO Rep. 2:376–381; Isreal, D. A., N. Salama, U. Krishna, U. M. Rieger, J. C. Atherton, S. Falkow, and R. M. Peek. 2001. *Helicobacter pylori* genetic diversity within the gastric niche of a single human host. Proc. Natl. Acad. Sci USA. 98:14625–14630, all of which are incorporated by reference herein).

It was determined among natural infecting populations of NTHi there exists a distributed gene pool, and the extent of the NTHi supra-genome was assessed. A highly redundant genomic library was constructed from the pooled DNA of ten otitis media isolates (one encapsulated and nine NTHi) and this library was used as a tool for identifying novel genes involved in biofilm formation and virulence. The ten clinical strains that comprised the pooled library underwent a minimal number of subcultures prior to the isolation of their genomic DNA. This ensured that there was essentially no decrease in selective pressure, which could result in the loss of particular contingency genes among the populations of cells in each isolated culture.

The sequence data indicate that a minimum of 9.3% of the analyzed clones from the 10 clinical strains contain substantial regions of DNA not present in the reference strain Rd. In a smaller study, Davis et al. (Davis, J., A. L. Smith, W. R. Hughes, and M. Golomb. 2001. Evolution of an autotransporter: domain shuffling and lateral transfer from pathogenic *Haemophilus* to *Neisseria*. J. Bacteriol. 183:4686–4635, incorporated by reference herein) obtained comparable results in which approximately 10% of the clones constructed from a pathogenic NTHi strain were novel relative to Rd. One finding from the sequence analysis was that 73% of the nonRd sequences identified consisted of newly identified loci that have no significant homologies to any known nucleotide sequences in any organism currently available in the public databases.

The distributed genome hypothesis states that the supra-genome of a given bacterial species includes a contingency gene pool from which each strain has a unique distribution when compared with all other strains composing the species. This is supported by the results obtained from the comparative analysis performed on the 10 strains used to construct the pooled genomic library as no two strains appeared to be any more related to each other than to the other eight, and each strain had a unique complement of the newly identified nonRd sequences. These distributed contingency genes, through reassortment during chronic infectious processes, provide for an increased number of genetic characters that enable the population as-a-whole to adapt rapidly to environmental factors such as those experienced in the host. A corollary to the distributed genome hypothesis is that genomic analysis of any one bacterial strain will not provide adequate information regarding the complete set of genes contributing to chronic pathogenicity. Genetic diversity in the form of genomic plasticity, wherein organisms of the same species display different genic complements (as opposed to allelic complements), forces a re-evaluation of the definition of a species, which now must be thought of as a population of organisms that all share a common core set of genes with each strain or isolate having a unique complement of contingency genes from a population-based supra-genome. Evidence has been accumulating from multiple groups of investigators who study chronic respiratory infections that multiple NTHi strains are often carried simultaneously by the host, and that there is extensive horizontal gene transfer among the several strains during chronic infections. In a study by Murphy et al. (Murphy, T. F., S. Sethi, K. L. Klingrman, A. B. Brueggemann, and G. V. Doem. 1999. Simultaneous respiratory tract colonization by multiple strains of nontypeable *Haemophilus influenzae* in chronic obstructive pulmonary disease: implications for antibiotic therapy. J. Infect. Dis. 180:404–409, incorporated by reference herein), it was reported that multiple strains of NTHi were present simultaneously in the sputum of 26.3% of adults with chronic obstructive pulmonary disease, and that these numbers likely underestimated the true frequency of the presence of multiple strains of NTHi as they had only sampled an average of 6.3 colonies per isolate. Genomic DNA typing revealed very extensive differences in PCR band patterns among all co-infecting strains as did OMP typing by SDS-PAGE, thus arguing strongly for multiple strain infections, as opposed to strain evolution in vivo. They further determined the MICs for 14 different antibiotics for each strain recovered, and observed in all cases very different MICs among the strains from a single clinical isolate.

In another series of studies, Smith-Vaughan et al. (Smith-Vaughan, H. C., K. S. Sriprakash, J. D. Mathews, and D. J. Kemp. 1995. Long PCR-ribotyping of nontypeable *Haemophilus influenzae*. J Clin Microbiol. 33:1192–1195; Smith-Vaughan, H. C., A. J. Leach, T. M. Shelby-James, K. Kemp, D. J. Kemp, and J. D. Mathews. 1996. Carriage of multiple ribotypes of non-encapsulated *Haemophilus influenzae* in Aboriginal infants with otitis media. Epidemiol. Infect. 116:177–183; Smith-Vaughan, H. C., K. S. Sriprakash, J. D. Mathews, and D. J. Kemp. 1997. Nonencapsulated *Haemophilus influenzae* in Aboriginal infants with otitis media: prolonged carriage of P2 porin variants and evidence for horizontal P2 gene transfer. Infect Immun. 65:1468–1474, all of which are incorporated by reference herein) described simultaneous carriage and horizontal gene transfer among multiple NTHi strains in Australian Aboriginals. In these studies they document numerous cases of horizontal transfer (among individual strains within infectious isolates) of the gene encoding the major outer membrane protein P2. These investigators state that the findings of identical P2 sequences in different genetic backgrounds, and dissimiliar P2 sequences in similar genetic backgrounds, suggest that horizontal gene transfers make a significant contribution to the diversity of *H. influenzae*. They further note that the evidence for horizontal gene transfer indicates that genes other than P2 are also subject to immune selection as otherwise there would be little advantage for a P2 variant in moving from one genetic background to another. They note that their analysis of *H. influenzae* strains from single chronically infected persons present a complex picture of multiple insertions, deletions and substitutions of amino acids, and that horizontal transmission of P2 gene segments provides the most likely mechanisms for genetic diversification. Moreover, they note that chronic infections which are associated with the carriage of large numbers of bacteria distributed among multiple strains would provide an environment that favored horizontal gene transfer, and the resultant reassortment would lead to long-term persistence of *H. influenzae* due to sequential carriage of recombinants with improved fitness. Finally, they state that their data favor P2 evolution by selection and provide no evidence of antigenic drift among sequential isolates. They concluded that horizontal gene transfer in *H. influenzae* was expected as these organisms are naturally competent, and that co-colonization with multiple types at the same time would provide the opportunity for gene transfer (Smith-Vaughan, H. C., K. S. Sriprakash, J. D. Mathews, and D. J. Kemp. 1997. Nonencapsulated *Haemophilus influenzae* in Aboriginal infants with otitis media: prolonged carriage of P2 porin variants and evidence for horizontal P2 gene transfer. Infect Immun. 65:1468–1474, incorporated by reference herein).

It is true that the above reports on NTHi evolution confine themselves largely to single gene systems, particularly those known to be involved with surface proteins. However, they do not favor the hypothesis that genetic variants have arisen primarily by point mutations, nor is there any reason to suppose a priori that similar horizontal gene transfer mechanisms are not operative over the entire *H. influenzae* genome as nearly all *H. influenzae* genes, including many of the novel sequences reported here, have USSs to aid in uptake, retention and transformation. Moreover, Ochman and Lawrence (Ochman, H., J. G. Lawrence, and E. A. Groisman. 2000. Lateral gene transfer and the nature of bacterial innovation. Nature 405:299–304, incorporated by reference herein) found that bacterial evolution occurs largely through horizontal gene transfer, and that this mechanism produces extremely dynamic genomes in which substantial amounts of DNA are introduced into and deleted from the chromosome. Lawrence (Lawrence, J. 2001. Catalyzing bacterial speciation: correlating lateral transfer with genetic headroom. Syst Biol. 50:479–496, incorporated by reference herein) further showed that the amounts of foreign DNA in bacterial genomes, and the rate at which this DNA is acquired, are consistent with gene transfer as the primary catalyst for microbial differentiation.

The finding that many natural NTHi infections are polyclonal, and that strains evolve in vivo (Murphy, T. F., S. Sethi, K. L. Klingman, A. B. Brueggemann, and G. V. Doem. 1999. Simultaneous respiratory tract colonization by multiple strains of nontypeable *Haemophilus influenzae* in chronic obstructive pulmonary disease: implications for antibiotic therapy. J. Infect. Dis. 180:404–409; van Alphen, L., D. A. Caugant, B. Duim, M. O'Rourke, and L. D. Bowler. 1997. Differences in genetic diversity of nonencapsulated *Haemophilus influenzae* from various diseases. Microbiology 143:1423–1431, both of which are incorporated by reference herein), suggests that during chronic infections the horizontal reassortment of genes from the infecting-population supra-genome may act as a supra-virulence factor. A supra-virulence factor is defined as a trait which exists at the population level, as opposed to the individual bacterial cell level, that provides for increased bacterial survival or pathogenicity at the expense of the host.

The extensive genomic-plasticity results reported herein support the concept that polyclonal NTHi infections would provide sufficient genomic fodder to allow for nearly limitless numbers of recombinants, both allelic and genic. Thus, with the generation of large numbers of recombinant bacteria, the probability would be greatly increased, when compared with a clonal infection, of a strain appearing that displayed a significant survival advantage for the environmental conditions encountered in a particular host. In fact, the use of clonal isolates for in vivo infection models may, in part, explain why it is often difficult to recapitulate chronic or persistent infections in experimental animals.

The data presented here supports the concept that the NTHi possess a population-based supra-genome and that no two strains have the same complement of genes. Moreover, it would appear as if the NTHI supra-genome is necessarily much larger in size than the genomes of individual bacteria.

The distributed genome hypothesis correlates well with the finding that chronic bacterial infections of the middle-ear and other organs are often associated with biofilm formation (Ehrlich, G. D., R. Veeh, X. Xang, J. W. Costerton, J. D. Hayes, F. Z. Hu, B. J. Daigle, M. D. Ehrlich, and J. C. Post. 2002. Mucosal biofilm formation in middle-ear mucosa in the chinchilla model of otitis media. JAMA 287:1710–1715; Post, J. C. 2001. Direct evidence of bacterial biofilms in otitis media. Laryngoscope 111:2083–2094; Post, J. C., and G. D. Ehrlich. 2000. The impact of the polymerase chain reaction in clinical medicine. JAMA 283:1544–1546; Rayner, M. G., Y. Zhang, M. C. Gorry, Y. Chen, J. C. Post, and G. D. Ehrlich. 1998. Evidence of bacterial metabolic activity in culture-negative otitis media with effusion. JAMA 279:296–299, all of which are incorporated by reference herein), as biofilms are known to provide a fertile environment for horizontal gene transfer (Hausner, M., and S. Wuertz. 1999. High rates of conjugation in bacterial biofilms as determined by quantitative in situ analysis. Appl. Environ. Microbiol. 65:3710–3713, incorporated by reference herein). Moreover, it has recently been suggested that DNA is a major component of the extracellular biofilm matrix of the gram-negative opportunistic pathogen *Pseudomonas aeruginosa* (Whitchurch, C. B., T. Tolker-Nielsen, P. C. Ragas, and J. S. Mattick. 2002. Extracellular DNA required for bacterial biofilm formation. Science 295:1487, incorporated by reference herein). An understanding of the extent of genomic plasticity in bacterial pathogens such as NTHi and *P. aeruginosa* should provide insight into clinically relevant topics such as biofilm development and expression of virulence factors.

Claverys et al. (Claverys, J. P., M. Prudhomme, I. Mortier-Barriere, and B. Martin. 2000. Adaptation to the environment: *Streptococcus pneumoniae*, a paradigm for recombination-mediated genetic plasticity? Mol Microbiol. 35:251–259, incorporated by reference herein) have independently put forth a theorem of bacterial diversity from their studies of the gram-positive *Streptococcus pneumoniae* that incorporates some of the same emergent concepts developed hereby studying the gram-negative pathogens *H. influenzae* (vidae supra) and *Pseudomonas aeruginosa* (data not shown). In their model, substitutive recombination among DNAs from other pneumococci is the most common form of gene acquisition. However, they also recognize diversity generation through insertion of capsular genes and the creation of mosaic genes through iterative homologous recombination events. These investigators state that, through transformation, each pneumococcus has access to a 'global' genome that is larger than the genome of any single bacterium. They go on to estimate that the global genome may be approximately 0.5 Mb larger than a single bacterium's. Thus, they understand the issue, but without the large-scale genomic comparative data contained in this report, they were not able to fully appreciate the extent of genomic plasticity nor the size and scope of the supra-genomic reservoir.

It is maintained that the degree of plasticity among strains of *H. influenzae* is considerably greater than what is reported. More stringent requirements were imposed on the sequences that were classified as novel than for those classified as Rd. Seemingly novel clones were knowingly excluded either because their internal sequences could not be obtained easily or because the level of ambiguity in their sequences was >5% over the length of the cloned fragment. Moreover, isolates were analyzed that were collected from one infection site, the middle ear, and in one geographical location. An even higher percentage of novel DNA sequences likely would be detected among strains acquired from a variety of infection sites and from healthy carriers. Indeed, van Alphen et al. (van Alphen, L., D. A. Caugant, B. Duim, M. O'Rourke, and L. D. Bowler. 1997. Differences in genetic diversity of nonencapsulated *Haemophilus influenzae* from various diseases. Microbiology 143:1423–1431, incorporated by reference herein) reported that the genetic diversity of NTHi strains taken from patients with otitis media is less than that seen in strains isolated from healthy carriers or from patients with chronic disease.

A number of sequences already known to contribute to *H. influenzae* pathogenesis emerged in the set of contingency genes, including those required for tryptophan catabolism and for the biosynthesis of various adhesins. Also, proteins from phage and restriction/modification (R/M) systems constitute 22% of the homologs listed in Table 4, as phage are often associated with horizontal gene transfer (Dobrindt, U., and J. Hacker. 2001. Whole genome plasticity in pathogenic bacteria. Curr. Opin. Microbiol. 5:550–557; Hacker, J., G. Blum-Oehler, I. Mühldorfer, and H. Tschäpe. 1997. Pathogenicity islands of virulent bacteria: structure, function and impact on microbial evolution. Mol. Microbiol. 23:1089–1097, both of which are incorporated by reference herein), and R/M gene clusters are emerging as part of the flexible gene pool of a prokaryotic genome (Hacker, J., and E. Carniel. 2001. Ecological fitness, genomic islands and bacterial pathogenicity: a Darwinian view of the evolution of microbes. EMBO Rep. 2:376–381; Kobayashi, I., A. Nobusato, N. Kobayashi-Takahashi, and I. Uchiyama. 1999. Shaping the genome: restriction-modification systems as mobile genetic elements. Curr. Opin. Genet. Dev. 9:649–656, both of which are incorporated by reference herein). Yet the majority of the homologies displayed by the putative products of the nonRd sequences Were to a wide array of proteins found not only in bacteria, but also in protozoans, metazoans, viruses and fungi.

Also as part of the support for a *Haemophilus* supra-genome theory, codon usage was used to determine whether the nonRd DNA sequences evidenced patterns typical of *Haemophilus*. These unique sequences, assuming a maximum parsimony model, can be attributed to at least three subsets. The first are those that are Haemophiloid in nature, meaning that both their G+C content and their codon usage are most similar to *Haemophilus* when compared against 71 diverse prokaryotic and eukaryotic genomes. This suggests that many of these newly identified contingency genes have been evolving within the *Haemophilus* supra-genome for very extended periods of time. Often this was the case even when the nucleotide- and/or protein-level homologies strongly implied that the sequence was similar to one in a distantly related organism. Of course, a number of sequences in this category may have been acquired more recently through horizontal transfer from a closely related bacterium. The second subset of unique sequences are those that display a G+C content similar to *Haemophilus*, but a codon usage not fitting the general *Haemophilus* pattern. These sequences have likely been in the *Haemophilus* supra-genome for an intermediate period of time and likely are examples of DNA in a state of codon flux following horizontal transfer. The third subset of unique sequences most likely represent additions to the *Haemophilus* supra-genome from distantly related organisms, as they differ both in terms of G+C content and codon usage. The hifD allele is found in this category, which may suggest that the hif pathogenicity island is relatively new to the *H. influenzae* supra-genome. Of course, there may be specific situations in which an uncharacteristic codon usage is acceptable or even advantageous to the organism (Hacker, J., and J. B. Kaper. 1999. The concept of pathogenicity islands, p. 1–11. In J. B. Kaper, and J. Hacker (ed.), Pathogenicity islands and other mobile virulence elements. American Society for Microbiology, Washington, D.C.; Moszer, I., E. P. C. Rocha, and A. Danchin. 1999. Codon usage and lateral gene transfer in *Bacillus subtilis*. Curr. Opin. Microbiol. 2:524–528, both of which are incorporated by reference herein). Overall, these subsets strongly indicate that *Haemophilus* is constantly acquiring new DNA sequences and that the contingency pool is, indeed, dynamic.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An isolated DNA sequence of *Haemophilus influenzae* clone 125_L2 shown in SEQ. ID. NO. 2.

* * * * *

SEQUENCE LISTING

<160> NUMBER OF SEQ ID NOS: 4

<210> SEQ ID NO 1
<211> LENGTH: 1656
<212> TYPE: DNA
<213> ORGANISM: Haemophilus influenzae
<220> FEATURE:
<221> NAME/KEY: misc_feature
<222> LOCATION: (1631)..(1631)
<223> OTHER INFORMATION: n is a, c, g, or t
<220> FEATURE:

```
<221> NAME/KEY: misc_feature
<222> LOCATION: (1634)..(1634)
<223> OTHER INFORMATION: n is a, c, g, or t

<400> SEQUENCE: 1
aagtaatatc acaatagsgg atccacgagc ttctattagg tatcgtattg gctgcagagg      60
gatatccaaa ggattatcgc aaaggcgatg aaatcagcgg attgcctaaa agtgcggtca     120
aaaacgagaa agttttctta gcgggtgtcg cagaacaaga aggcaagcta gtcacaaacg     180
gcggtcgtgt actttgtgtg actgcgttag gcgaaagtgt atttgaagca caacaaaaag     240
cgttaaaatt ggctgagcaa attcaatggt ctgggcgttt ttatcgtcga cattggtt       300
acagggctgt ggaacgagaa caagcaaaat agttagaaat cttgttgaat ttaattagat     360
aaaaaatatt gtacagggta gaattgtatt ttcctaggat ttaggatttt gttagggcaa     420
cgtttacgat tgctctgaca ataaattaga attattattt ttgttacttt atgaggttat     480
atcaacttat gcgacaattt gtcatcgtag tattatattc tgcaattctt ctttcattag     540
aagttattta tagaaaatta tttaatattt ctagtattga gagatacact gaaagttatt     600
tgtctgtttg tttgtttgtt tgtttgtttg tttttcaaa atatagaatt acaagaatat      660
tagttggcgc tttatttgca ataagtattg ttgttaataa tgtacattat gcagtatacc     720
aatcttggat tggacctgtt aattactcac ttgcatttaa agaaattaat gagataacaa     780
atgctggctt aacaatgata gataaattca tatatccatt gttatttggt ttatttgaag     840
ttgctgtgtt tttaagttta agtttcataa aaagaaaagt atataaactt tcttggattt     900
ttgactttat tttttatgct gtgatgatgt atgttttttgt tcgagcgtat acaacaaaat    960
cccatgagcg ttttatttca cctaacactg tttattctcg attaaaatcc aattatttat    1020
cgttgggtta tttatagga cgaattgttc cttatgagat attttcttta tctaatattc     1080
ctctttatca taaatctaag cctatgaaat cgggctctcc gvaaaattma rgaatataat    1140
tttaattaat gggggaaagt gcgacctcaa gtcattttag tgcttttggt tacgggagaa    1200
aaacatctcc tttttagat agcttaaaat ataaatcagg agctcttgtt ggtaaaactt     1260
attcaggagg aaagctaaca gcaatttctt taccaatgtt tttaatgca atyccttayc     1320
caaatggaat acaacagata gctaaaggag atacgaattt atttaattta gcgaaagagc    1380
aaggctttca gacatatttt tattcagctc aagctaggga tgatatgcat atgatcaatt    1440
ttttaggagg agcttggatt gatgatattc gttttccaga taatgaaggg tattctttaa    1500
gagattcaat gcctgataat aaattacttc ctgcttttaa aaatattaat ttagataatg    1560
gttatcattt tgttgttta catcatagag ggagtcatat tccctatggg gcattattag     1620
aatgaaaaag nagnaaggtg ttkggaaraa ataacg                              1656

<210> SEQ ID NO 2
<211> LENGTH: 1802
<212> TYPE: DNA
<213> ORGANISM: Haemophilus influenzae
<220> FEATURE:
<221> NAME/KEY: misc_feature
<222> LOCATION: (572)..(572)
<223> OTHER INFORMATION: n is a, c, g, or t

<400> SEQUENCE: 2
cctgcaacag ctagctgaga tgatacaacc gatcccgata aaactctgga tggtctaatt      60
ccagattctt ttgcaacttc agcaatgaca ggtaatgtag aaaaaacaat aaatccagta     120
cctgcaaaaa tggtcattaa ccaagtaatc attggcgcaa taaaatttat atgtttgggr     180
```

-continued

```
tttttacgsa ttaatctttc tgcataatta actaagratg ccattccccc tgtagcttgc      240
aatgttgctg ctgraagrgr tacagacatt atgrtcaaaa taacatctat tggracagrt      300
cctattggta gtcttaaacc caacgttaag rtagcaagtc caagaccacc aaataaacca      360
atggcaatac ctccaaatct aaggccaagt acaatagagg ctagarcaac aaaratttca      420
acccmgacca taatcatctc cttaatcaat gagtttgata ccaacgmata gcagctctaa      480
ctaatgctgc tgtagartcc tcataaagta taggttgctc tctcattgca ttttttagga     540
tcartgggat ttccgtacac cctagaataa tnacttctga accgtgacga ataagttcat      600
cacgttgtat taacattaat tcttcagctt tttgaatctc tccgctctta tataaataaa      660
tactttccat gaccgatttt tgatgttctt cattgggaag aagacaaatt aattccatat      720
ttttctaatg ttttctgata tagctttgtt gctaaagtag catcagtagc aagaatacca      780
atctttgttt tacccatttg tagaacttca ttaattgttg aatcaataat atttaacata      840
tcaacatgac atttctcttt tagttcatca taccaataat gtgcagtatt acaggcaatt      900
aggatacatt tagcacccgc attttctaac ccataaatgc gttcctccat tgcaagtagt      960
ggtgattctc ctccatgcaa aatggaagtt gtacgatcgg gaatatcagg aatagacgaa     1020
ataacaagag gaatatgttc ttgatcacaa tgagctggtg taaattgaat aaatttctga     1080
aacatatctg ccgttgctgc tggtcccatt ccacctaaaa taccaataat gttcttcata     1140
agaaaaattc tcctatttat ctttgggtta tttattttta acaaaatcta atgaaataag     1200
agaaatgcaa caaatcgcac gccaatgcaa atattgcata gcataaattg cgcacattac     1260
aaatgtacaa aataatgatt caaatcaata tgataaaaaa caaaaagtga taagctatta     1320
catatttaag aataaggtat gcaaaattag catagagaga ataataaat gaaaatatt        1380 gaaacaaaat ggtkagaaga tbttttaata ctggaagata cacgcaattt ttcacaggca     1440
gcagaacata gaaatttatc gcaatcagct tttagccgga gaataatttc tcttgaagaa     1500
tctattggtg taaaacycty cgatagaycc tctgycccac ttcaacttac agaagaagga     1560
aaattatttc atycgcaagc tagaaaacctt ttaaaacagt tacagtataa tcttgatgaa    1620
ttattagggc agaatacaca aaaaaaaccg aatataactt ttgcagctgc acattcccta     1680
tctttatctg taatgccaaa gttaattcat gatattggtc aatcacacca gaactttatt     1740
tattccgttg aagcaattga tgttgatcaa acagtaaaaa ctttggttga aggaaaaagt     1800
ga                                                                    1802
```

<210> SEQ ID NO 3
<211> LENGTH: 950
<212> TYPE: DNA
<213> ORGANISM: Haemophilus influenzae
<220> FEATURE:
<221> NAME/KEY: misc_feature
<222> LOCATION: (15)..(15)
<223> OTHER INFORMATION: n is a, c, g, or t

<400> SEQUENCE: 3

```
tggaagtgat gctcnacccc gaccggacat tgtgggtgga tcggctgtcg tctggccgtg       60
cgccgctcgg cgtcgaactg cccgaagccg atggcgaacg catcatccgc ctggtcgccg      120
cccatgtcgg tgcggaggtg catcgcggcc aaccgctctt gaccgccgaa ctgcctgaaa      180
ccggcgaacg cttcgagggc atcctgccgc ccgccgcacc cggccgcc   cggccttttgc     240 gctgcgcaag cgtgccgtga gcatcatcgg tctggatcgc tatgtggctg atggcatcct      300
```

-continued

| | |
|---|---|
| gaccactggg caggccgagt ttctgcgtca tgccgtgcgc gagcggcaca acatcctgat | 360 |
| cgccggaggc accagcaccg gcaagaccac gctggccaat gccttgctgg ccgagatcgc | 420 |
| cgccaccggc gaccgcgtgc tggtgctcga agacaccatc gaactgcaat gcgcggcccg | 480 |
| cgaccatgtg ccgctgcgca cccgcgccgg cgtcgtgtcc atgaccgagc tggtgcgggc | 540 |
| cacgatgcgc ctgcggcccg accgcgtgat cgtcggcgaa gtgcgcggcg gcgaagcgct | 600 |
| ggatctggtg aaggtctggg gcaccggcca ccccggcggc atcgccacca ttcatgccgg | 660 |
| ctccgcgttg ggcgcgctgc tgcgcctgga gcaactgatc ctcgaagtgg cggtgaatcc | 720 |
| gccccgcgcc ctgatcgccg aggcggtcaa tgtcgtgatc cacatcgcag gccgcggccg | 780 |
| caagcgccac gtcgaaacca tttcccgcgt cgtcggtttc gacggcgcgg gctaccgcct | 840 |
| ggcggatgcg ctggaagcga cgcttcccga gctgccgccg gttcctctta cagccgctgc | 900 |
| cgctacgcct tcctcgatcc ctgaacaacc tggagaactg ccatgacgca | 950 |

<210> SEQ ID NO 4
<211> LENGTH: 2597
<212> TYPE: DNA
<213> ORGANISM: Haemophilus influenzae
<220> FEATURE:
<221> NAME/KEY: misc_feature
<222> LOCATION: (883)..(883)
<223> OTHER INFORMATION: n is a, c, g, or t

<400> SEQUENCE: 4

| | |
|---|---|
| tttgattgag ctcacgatat ttatcacacc cttcttgact acgtagatcg caagccatgc | 60 |
| catagtaaga tttagctttt tgctcatctt tataaagaaa cgcgttccct aattccacaa | 120 |
| acactgcagg atcttggcta ttttccaatt ctaattgcaa tgtttcaaat tttgctttta | 180 |
| catcatcatt cggcgcctca tcttttaatt tttttaattt tattaacttc acctttgtac | 240 |
| caatcactgt catttcatct ttagtttctt tattatgctc ttgcaataat tgctcggctt | 300 |
| tattttcatc ttttaccgtg ccaattccca aaatataaag aatagctaat tcacgataaa | 360 |
| cgctatttgg acgaaatcga ttattttcta cttgtctaaa caccgcaggt tgatggtgta | 420 |
| atagactgct tttataggct ttatccaacc aataaaacgc cttttcccaa tctggtttaa | 480 |
| tattatcatt accatcaaaa taccaacgcc ctaactgtgc ttccgccatt ggataaccat | 540 |
| tatttgcggc ttgttccacc aacatataac ctgtcaaaaa atccttatcc ttatttacgg | 600 |
| catctatagm caagaatcat tttggcaaaa ttatcgcccg catccgcagc cattttcata | 660 |
| taatgttttg acgattcttt atttccttg tcattataaa tggttgccaa accacgatat | 720 |
| gccaacggat aattttgatt gctggcttta agaaaccact ctgtcgctaa attttttga | 780 |
| cctwtgataa aataataacg ccccaactga tattgcgtca cagcattgcc ttttcatgc | 840 |
| caacactcgc aaacgtgctg gagaaaaatc ttcaagtgct ttntctagct tgctgatcgc | 900 |
| cataatactc ctgagcacta actaatmvtt ctagctgttt aatctcacga tattctgggt | 960 |
| aatattgggt aaaatacaca gctccaccac caattactgc caataataaa acggctaagg | 1020 |
| ttaattttt cttcattatt ttgttccttg atttaattgt ttatacatct cacaacccttt | 1080 |
| ttgctcttta ttatcacaag ccttgccaaa ccattttttg gcagtggcaa aatttttgttt | 1140 |
| tactcctatt ccgccatatt aagcaagacc aactattgcc tgcgctcgag aattattatt | 1200 |
| ttctgctgct ttttgatacc attttatggc ttcagtttta ttttctttta ctccatcgcc | 1260 |
| atcataatac atatcgccca atatcatttg ggattcagta tcattttgat ttgccgcttt | 1320 |
| tttcaaccat ttcactgctt ccgtattatt ctgttttacg ccaactccat ctttatacat | 1380 |

```
cattcccact ttaaattggg catcaacatc atcttgctcc gcagcttcct tcaaccattt    1440
aaagccttct tggtaatttt gttttacgcc caagccgtta atatacatac cagctaaatc    1500
atattgagcg atacgtacac cttgttcagc cgattttta taccatttta tcgcttcaaa    1560
ataatcttgc tttatgccat cgccattttt atataacacc gctaacatcc cctgtgcaat    1620
cccatctccc tgctctgcta aaggacgaat aattgctaat gcggacttaa aatctttctg    1680
ttcaaataaa tgaacaatct tatcaacttg ctcctcttcc attgcataaa cggttgattg    1740
aaaagaaaag atagaagcac cgaaaagtgc ggtggtaaga agtgtttttg ttagtttcat    1800
tttgttttcc tattaaattg aatgaataaa taatctttta tttttattca ctaaaattgg    1860
cgtataagta gaaaaatctt taagtacttc gctatgtggg tgcccatttc gtcgctggct    1920
atctgctgaa aacacactaa gacaaggcga aaatatgttc gctaatcctt gctgccaatt    1980
atgctttgaa ccgtgatggg gaacttgtaa gcmatmaaty stsgccattc gttctacacc    2040
taatgattgc gttaaatcgg ttaataatgg caaatcattt aaaaacgcat cgcctgtata    2100
taaaatcgca tttttgtttc tatcttttgg gaaaacaaga atttcatttc catcattttt    2160
aggaatatca taaatataat tattccctag tccccaaaca gctgttgatg ttatatttct    2220
aatatataaa tattgagaaa tgatatttt gttttattt ccatttccaa atgcgagagt    2280
atagagtgtt tttaaggctg gcgttggatc tgtggaatta gactgatgag attgaataat    2340
ttgctcaacc tgcttttgaa aagcagtcaa atttgttggc acttttgcaa gcaaatgaaa    2400
tggcacgtta tataaaacaa attcaaactg ctcttcgcct tttctaaata aaagggcttt    2460
atcaggattg agccaatgta cattttgttt taagttatca aactcatttg ataattttc     2520 agtagtttta aaagaaagta catcatcaaa attacttggt tcaagagtta tcaaaatttc    2580
actctcattt tcttttg                                                   2597
```